United States Patent
Yang

(10) Patent No.: US 9,629,867 B2
(45) Date of Patent: Apr. 25, 2017

(54) METHODS AND COMPOSITIONS OF IMPROVED MODIFIED SIRNA

(71) Applicant: AM Biotechnologies LLC, Houston, TX (US)

(72) Inventor: Xianbin Yang, Houston, TX (US)

(73) Assignee: AM Biotechnologies, Inc., Houston, TX (US)

( * ) Notice: Subject to any disclaimer, the term of this patent is extended or adjusted under 35 U.S.C. 154(b) by 0 days.

(21) Appl. No.: 14/645,351

(22) Filed: Mar. 11, 2015

(65) Prior Publication Data

US 2015/0322431 A1 Nov. 12, 2015

Related U.S. Application Data

(60) Provisional application No. 61/951,518, filed on Mar. 11, 2014.

(51) Int. Cl.

| | |
|---|---|
| A61K 48/00 | (2006.01) |
| C12N 15/11 | (2006.01) |
| C07H 21/02 | (2006.01) |
| C07H 21/04 | (2006.01) |
| A61K 31/713 | (2006.01) |
| A61K 45/06 | (2006.01) |
| C12N 15/113 | (2010.01) |

(52) U.S. Cl.
CPC ............ *A61K 31/713* (2013.01); *A61K 45/06* (2013.01); *A61K 48/00* (2013.01); *C12N 15/111* (2013.01); *C12N 15/113* (2013.01); *C12N 2310/14* (2013.01); *C12N 2310/313* (2013.01); *C12N 2310/321* (2013.01); *C12N 2310/335* (2013.01); *C12N 2310/344* (2013.01); *C12N 2310/50* (2013.01); *C12N 2320/31* (2013.01); *C12N 2320/50* (2013.01); *C12N 2320/51* (2013.01); *C12N 2320/52* (2013.01)

(58) Field of Classification Search
USPC .......................................... 536/24.5; 514/44
See application file for complete search history.

(56) References Cited

PUBLICATIONS

Prakash et al. (J. Med. Chem., 2005 vol. 48:4247-4253).*
Yang et al. (ACS Chem. Biol., 2012 vol. 7:1214-1220).*
Nishimura et al. (Cancer Discovery, ePub Sep. 3, 2013, vol. 11:1302-1315).*
Wang et al. (Molecular Medicine Reports, 2015 vol. 11:924-930).*
Wu et al. (Nature Communications, Mar. 12, 2014 vol. 5:1-12).*

* cited by examiner

*Primary Examiner* — Terra C Gibbs
(74) *Attorney, Agent, or Firm* — Blank Rome LLP

(57) ABSTRACT

Chemically modified small interfering RNAs (siRNAs) that include both phosphorodithioate modifications (PS2-RNA) and 2'-O-methyl modifications (MePS2) provide improved RNA silencing. Specific chemically modified siRNA that show enhanced silencing of RNAs involved in resistance to chemotherapeutic agents are provided.

20 Claims, 16 Drawing Sheets

Synthesis of thiophosphoramidites 1a–d: (i) tris-(pyrrolidino)phosphine, 1H-tetrazole;
(ii) 1-(trimethylsilyl)imidazole; (iii) ethanedithiol monobenzoate, 1H-tetrazole.
Abbreviations: $B^Z$ = $Ade^{Bz}$(a), $Cyt^{Ac}$(b), $Gua^{Ac}$(c), Ura (d);
DMT = dimethoxytrityl;
Ph = phenyl;
TBDMS = tert-butyldimethylsilyl

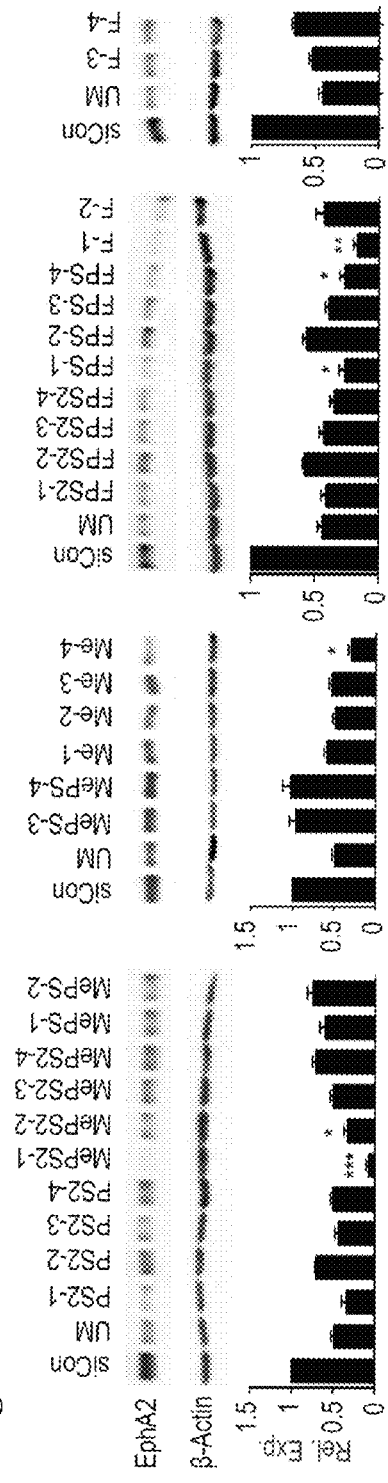
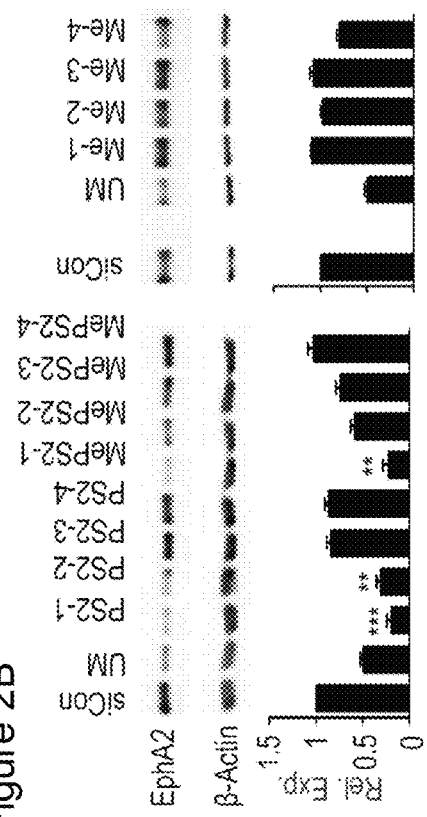
Figure 2A
Figure 2B

Figure 2H

```
            S   5'-U  GAC_MeS2AU    GCCGAUCU_MeS2AC_MeS2AU_MeS2G_MeS2TT-3'
                SEQ. ID. 77
MePS2-5
            AS  3'-TTA_MeS2CUG   UA_MeS2CGGCUAGA   UG  UA   C-5'
                SEQ. ID. 79

S   5'-U  GAC_MeS2AUGCCGAUCU_MeS2AC_MeS2AU_MeS2G_MeS2TT-3'
                SEQ. ID. 77
MePS2-6
            AS  3'-TTA_MeS2CUG   UACGGCUAGA   UG  UA   C-5'
                SEQ. ID. 79

S   5'-U  GAC_MeS2AUGCCGAUCU_MeS2ACAU_MeS2G_MeS2TT-3'
                SEQ. ID. 80
MePS2-7
            AS  3'-TTA_MeS2CUG   UACGGCUAGA   UGUA   C-5'
                SEQ. ID. 79

S   5'-U  GAC_MeS2 AUGCCGAUCUACAU_MeS2G_MeS2TT-3'
                SEQ. ID. 81
MePS2-8
            AS  3'-TTA_MeS2CUG   UACGGCUAGAUGUA   C-5'
                SEQ. ID. 79

S   5'-UGAC_MeS2AUGCCGAUCU_MeS2ACAU_MeS2G_MeS2TT-3'
                SEQ. ID. 80
MePS2-9
            AS  3'-TTACUG   UACGGCUAGA   UGUA   C-5'
                SEQ. ID. 28
```

Figure 2I

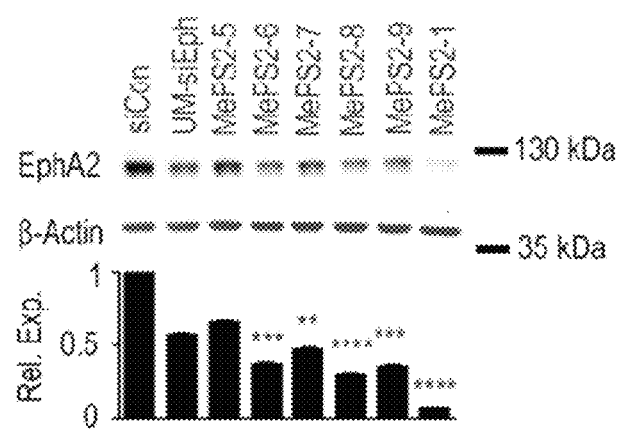

Figure 3E
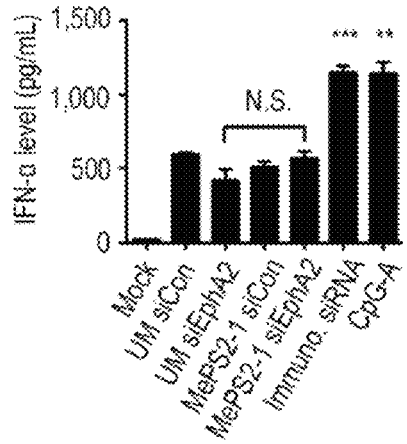
Figure 3F     1.25 µg siRNA
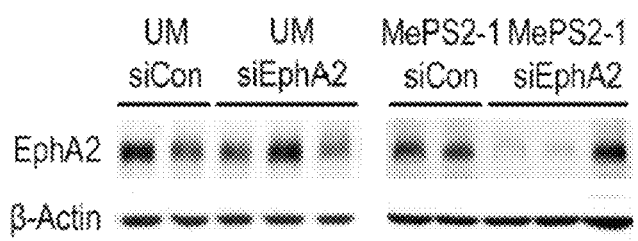
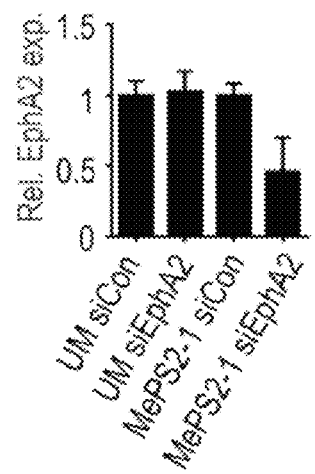
2.5 µg siRNA
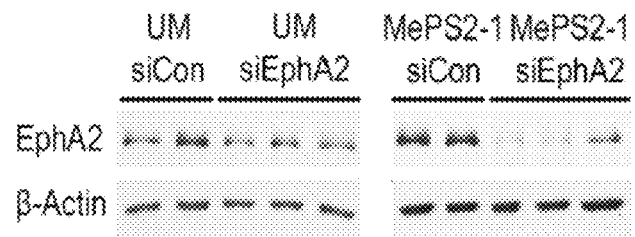
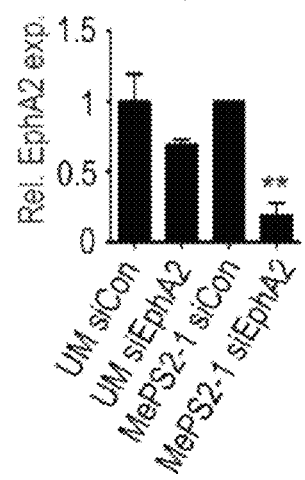

Figure 8

Selected crystal data and refinement parameters for PS2- and MePS2-modified RNAs

| Structure | CPs2G-RNA | AMePs2A-RNA | AMePs2G-RNA |
|---|---|---|---|
| Crystal data | | | |
| Space group | | Monoclinic C2 | |
| Unit cell constants | | | |
| $a$ [Å] | 40.93 | 41.18 | 40.91 |
| $b$ [Å] | 35.02 | 35.05 | 34.84 |
| $c$ [Å] | 31.87 | 31.85 | 32.27 |
| $\beta$ [deg] | 128.8 | 128.7 | 127.5 |
| No. of strands per asym. unit | 1 | 1 | 1 |
| No. of unique reflections | 11,133 | 11,706 | 12,267 |
| Resolution [Å] (last shell) | 1.19 (1.23-1.19) | 1.18 (1.22-1.18) | 1.13 (1.17-1.13) |
| Completeness [%] (last shell) | 97.7 (88.5) | 99.9 (100) | 95.5 (90.7) |
| R-merge [%] (last shell) | 5.0 (4.2) | 8.2 (21.6) | 5.3 (25.5) |
| Refinement | | | |
| R-work / R-free | 0.139 / 0.183 | 0.160/0.201 | 0.181/0.208 |
| No. of RNA atoms | 256 | 258 | 258 |
| No. of water molecules | 97 | 70 | 52 |
| No. of metal ions | 2 $Sr^{2+}$ [a] | - | - |
| R.m.s. deviations: | | | |
| Bond lengths [Å] | 0.012 | 0.011 | 0.012 |
| Bond angles [Å] [b] | 0.03 | 0.036 | 0.040 |
| Data deposition | | | |
| PDB ID | 4RBY | 4RBZ | 4RC0 |

[a] Refinement suggested $Sr^{2+}$ ions with occupancy 0.3. This is in contrast to the crystallization conditions
[b] 1...3 distance based on SHELX refinement.

Figure 9A
Figure 9B
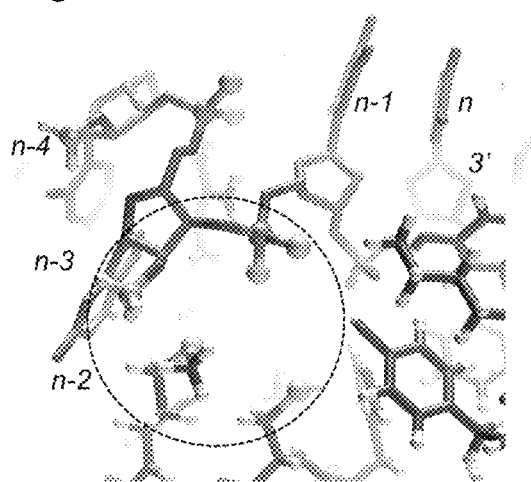
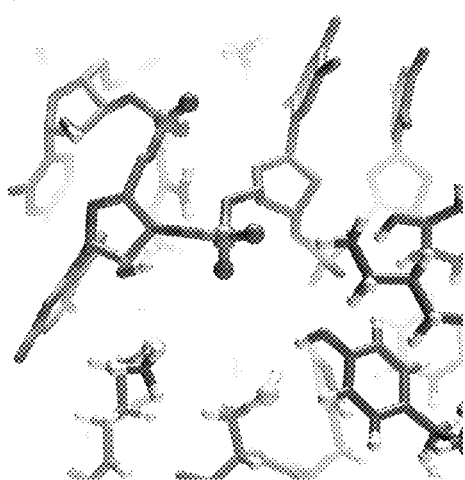

SEQUENCE LISTING

```
<160> NUMBER OF SEQ ID NOS: 81

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1
aaucagauug aaccuucaut t                                             21

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
ttuuagucua acuuggaagu a                                             21

<210> SEQ ID NO 3
<211> LENGTH: 21
<212> TYPE: DNA
<213> ORGANISM: Artificial Sequence
<220> FEATURE:
<223> OTHER INFORMATION: siRNA
```

```
<400> SEQUENCE: 3
acaugaagca gcacgacuut t                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
ttuguacuuc gugcugcuga a                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (19)..(19)
<223> OTHER INFORMATION: phosphorodithioate modification

<400> SEQUENCE: 5
acaugaagca gcacgacuut t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: phoshorodithioate modification

<400> SEQUENCE: 6
acaugaagca gcacgacuut t                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (20)..(20)
<223> OTHER INFORMATION: phosphorodithioate modification

<400> SEQUENCE: 7
ttuguacuuc gucgugcuga a                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (19)..(20)
<223> OTHER INFORMATION: phosporodiothioate modification

<400> SEQUENCE: 8
```
ttuguacuuc gucgugcuga a                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: Phosphorodithioate modification
<220> FEATURE:
<221> NAME/KEY: modified_base
<222> LOCATION: (7)..(7)
<223> OTHER INFORMATION: Phosphorodithioate modification
<220> FEATURE:
<221> NAME/KEY: modified_base
<222> LOCATION: (11)..(11)
<223> OTHER INFORMATION: Phosphorodithioate modification
<220> FEATURE:
<221> NAME/KEY: modified_base
<222> LOCATION: (15)..(15)
<223> OTHER INFORMATION: Phosphorodithioate modification
<220> FEATURE:
<221> NAME/KEY: modified_base
<222> LOCATION: (19)..(19)
<223> OTHER INFORMATION: Phosphorodithioate modification

<400> SEQUENCE: 9
acaugaagca gcacgacuut t                                              21

<210> SEQ ID NO 10
<211> LENGTH: 20
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: Phosphorodithioate modification
<220> FEATURE:
<221> NAME/KEY: modified_base
<222> LOCATION: (7)..(7)
<223> OTHER INFORMATION: Phosphorodithioate modification
<220> FEATURE:
<221> NAME/KEY: modified_base
<222> LOCATION: (12)..(12)
<223> OTHER INFORMATION: Phosphorodithioate modification
<220> FEATURE:
<221> NAME/KEY: modified_base
<222> LOCATION: (18)..(18)
<223> OTHER INFORMATION: Phosphorodithioate modification

<400> SEQUENCE: 10
acaugaagca gacgacuutt                                                20

<210> SEQ ID NO 11
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<220> FEATURE:
<221> NAME/KEY: modified_base
<222> LOCATION: (11)..(11)
<220> FEATURE:
<221> NAME/KEY: modified_base
<222> LOCATION: (19)..(19)

```
<400> SEQUENCE: 11
acaugaagca gcacgacuut t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(10)
<223> OTHER INFORMATION: Phosphorodithioate modification
<220> FEATURE:
<221> NAME/KEY: modified_base
<222> LOCATION: (19)..(19)
<223> OTHER INFORMATION: Phosphorodithioate modification

<400> SEQUENCE: 12
acaugaagca gcacgacuut t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: Phosphorodithioate modification
<220> FEATURE:
<221> NAME/KEY: modified_base
<222> LOCATION: (10)..(10)
<223> OTHER INFORMATION: Phosphorodithioate modification

<400> SEQUENCE: 13
acaugaagca gcacgacuut t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: Phosphorodithioate modification
<220> FEATURE:
<221> NAME/KEY: modified_base
<222> LOCATION: (9)..(9)
<223> OTHER INFORMATION: Phosphorodithioate modification
<220> FEATURE:
<221> NAME/KEY: modified_base
<222> LOCATION: (15)..(15)
<223> OTHER INFORMATION: Phosphorodithioate modification
<220> FEATURE:
<221> NAME/KEY: modified_base
<222> LOCATION: (20)..(20)
<223> OTHER INFORMATION: Phosphorodithioate modification

<400> SEQUENCE: 14
ttuguacuuc gucgugcuga a                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA
```

```
<220> FEATURE:
<221> NAME/KEY: modified_base
<222> LOCATION: (5)..(5)
<223> OTHER INFORMATION: Phosphorodithioate modification
<220> FEATURE:
<221> NAME/KEY: modified_base
<222> LOCATION: (12)..(12)
<223> OTHER INFORMATION: Phosphorodithioate modification
<220> FEATURE:
<221> NAME/KEY: modified_base
<222> LOCATION: (20)..(20)
<223> OTHER INFORMATION: Phosphorodithioate modification

<400> SEQUENCE: 15
ttuguacuuc gucgugcuga a                                                      21

<210> SEQ ID NO 16
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: Phosphorodithioate modification
<220> FEATURE:
<221> NAME/KEY: modified_base
<222> LOCATION: (20)..(20)
<223> OTHER INFORMATION: Phosphorodithioate modification

<400> SEQUENCE: 16
ttuguacuuc gucgugcuga a                                                      21

<210> SEQ ID NO 17
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (12)..(12)
<223> OTHER INFORMATION: Phosphorodithioate modification

<400> SEQUENCE: 17
ttuguacuuc gucgugcuga a                                                      21

<210> SEQ ID NO 18
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (11)..(11)
<223> OTHER INFORMATION: Phosphorodithioate modification

<400> SEQUENCE: 18
ttuguacuuc gucgugcuga a                                                      21

<210> SEQ ID NO 19
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (11)..(12)
```

<223> OTHER INFORMATION: Phosphorodithioate modification

<400> SEQUENCE: 19
ttuguacuuc gucgugcuga a                                          21

<210> SEQ ID NO 20
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (14)..(14)
<223> OTHER INFORMATION: Phosphorodithioate modification
<220> FEATURE:
<221> NAME/KEY: modified_base
<222> LOCATION: (19)..(19)
<223> OTHER INFORMATION: Phosphorodithioate modification

<400> SEQUENCE: 20
ttuguacuuc gucgugcuga a                                          21

<210> SEQ ID NO 21
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (19)..(19)
<223> OTHER INFORMATION: Phosphorodithioate modification

<400> SEQUENCE: 21
ttuguacuuc gucgugcuga a                                          21

<210> SEQ ID NO 22
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (14)..(14)
<223> OTHER INFORMATION: Phosphorodithioate modification

<400> SEQUENCE: 22
ttuguacuuc gucgugcuga a                                          21

<210> SEQ ID NO 23
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: Phosphorodithioate modification
<220> FEATURE:
<221> NAME/KEY: modified_base
<222> LOCATION: (11)..(11)
<223> OTHER INFORMATION: Phosphorodithioate modification

<400> SEQUENCE: 23
ttuguacuuc gucgugcuga a                                          21

-continued

```
<210> SEQ ID NO 24
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: Phosphorodithioate modification
<220> FEATURE:
<221> NAME/KEY: modified_base
<222> LOCATION: (9)..(9)
<223> OTHER INFORMATION: Phosphorodithioate modification

<400> SEQUENCE: 24
ttuguacuuc gucgugcuga a                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: Phosphorodithioate modification

<400> SEQUENCE: 25
ttuguacuuc gucgugcuga a                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (6)..(6)
<223> OTHER INFORMATION: Phosphorodithioate modification

<400> SEQUENCE: 26
ttuguacuuc gucgugcuga a                                              21

<210> SEQ ID NO 27
<211> LENGTH: 21
<212> TYPE: DNA
<213> ORGANISM: Artificial Sequence
<220> FEATURE:
<223> OTHER INFORMATION: siRNA

<400> SEQUENCE: 27
ugacaugccg aucuacaugt t                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA

<400> SEQUENCE: 28
ttacuguacg gcuagaugua c                                              21

<210> SEQ ID NO 29
<211> LENGTH: 21
<212> TYPE: DNA
```

```
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: Phosphorodithioate modification

<400> SEQUENCE: 29
ugacaugccg aucuacaugt t                                              21

<210> SEQ ID NO 30
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: Phosphorodithioate modification
<220> FEATURE:
<221> NAME/KEY: modified_base
<222> LOCATION: (12)..(12)
<223> OTHER INFORMATION: Phosphorodithioate modification

<400> SEQUENCE: 30
ugacaugccg aucuacaugt t                                              21

<210> SEQ ID NO 31
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: Phosphorodithioate modification

<400> SEQUENCE: 31
ttacuguacg gcuagaugua c                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: Phosphorodithioate modification
<220> FEATURE:
<221> NAME/KEY: modified_base
<222> LOCATION: (17)..(17)
<223> OTHER INFORMATION: Phosphorodithioate modification

<400> SEQUENCE: 32
ttacuguacg gcuagaugua c                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: MePS2 (phosphorodithioate phosphate and methyl
``` sugar modification)

<400> SEQUENCE: 33
ugacaugccg aucuacaugt t                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: MePS2 (phosphorodithioate phosphate and methyl
      sugar) modification
<220> FEATURE:
<221> NAME/KEY: modified_base
<222> LOCATION: (12)..(12)
<223> OTHER INFORMATION: MePS2 (phosphorodithioate phosphate and methyl
      sugar) modification

<400> SEQUENCE: 34
ugacaugccg aucuacaugt t                                              21

<210> SEQ ID NO 35
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: MePS2 (phosphorodithioate phosphate and methyl
      sugar) modification

<400> SEQUENCE: 35
ttacuguacg gcuagaugua c                                              21

<210> SEQ ID NO 36
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: MePS2 (phosphorodithioate phosphate and methyl
      sugar) modification
<220> FEATURE:
<221> NAME/KEY: modified_base
<222> LOCATION: (17)..(17)
<223> OTHER INFORMATION: MePS2 (phosphorodithioate phosphate and methyl
      sugar) modification

<400> SEQUENCE: 36
ttacuguacg gcuagaugua c                                              21

<210> SEQ ID NO 37
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: MePS1 (monothiophosphate and methyl sugar)
      modification -continued

```
<400> SEQUENCE: 37
ugacaugccg aucuacaugt t                                              21

<210> SEQ ID NO 38
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: MePS (monothiophosphate and methyl sugar)
      modification
<220> FEATURE:
<221> NAME/KEY: modified_base
<222> LOCATION: (12)..(12)
<223> OTHER INFORMATION: MePS (monothiophosphate and methyl sugar)
      modification

<400> SEQUENCE: 38
ugacaugccg aucuacaugt t                                              21

<210> SEQ ID NO 39
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: MePS (monothiophosphate and methyl sugar)
      modification

<400> SEQUENCE: 39
ttacuguacg gcuagaugua c                                              21

<210> SEQ ID NO 40
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: MePS (monothiophosphate and methyl sugar)
      modification
<220> FEATURE:
<221> NAME/KEY: modified_base
<222> LOCATION: (17)..(17)
<223> OTHER INFORMATION: MePS (monothiophosphate and methyl sugar)
      modification

<400> SEQUENCE: 40
ttacuguacg gcuagaugua c                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: methyl sugar modification

<400> SEQUENCE: 41
```
ugacaugccg aucuacaugt t								21

<210> SEQ ID NO 42
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: methyl sugar modification
<220> FEATURE:
<221> NAME/KEY: modified_base
<222> LOCATION: (12)..(12)
<223> OTHER INFORMATION: methyl sugar modification

<400> SEQUENCE: 42
ugacaugccg aucuacaugt t								21

<210> SEQ ID NO 43
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: methyl sugar modification

<400> SEQUENCE: 43
ttacuguacg gcuagaugua c								21

<210> SEQ ID NO 44
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: methyl sugar modification
<220> FEATURE:
<221> NAME/KEY: modified_base
<222> LOCATION: (17)..(17)
<223> OTHER INFORMATION: methyl sugar modification

<400> SEQUENCE: 44
ttacuguacg gcuagaugua c								21

<210> SEQ ID NO 45
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: phosphorodithioate phosphate and fluoride sugar
      modification

<400> SEQUENCE: 45
ugacaugccg aucuacaugt t								21

<210> SEQ ID NO 46
<211> LENGTH: 21

```
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: phosphorodithioate phosphate and fluoride sugar
      modification
<220> FEATURE:
<221> NAME/KEY: modified_base
<222> LOCATION: (12)..(12)
<223> OTHER INFORMATION: phosphorodithioate phosphate and fluoride sugar
      modification

<400> SEQUENCE: 46
ugacaugccg aucuacaugt t                                              21

<210> SEQ ID NO 47
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: phosphorodithioate phosphate and fluoride sugar
      modification

<400> SEQUENCE: 47
ttacuguacg gcuagaugua c                                              21

<210> SEQ ID NO 48
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: phosphorodithioate phosphate and fluoride sugar
      modification
<220> FEATURE:
<221> NAME/KEY: modified_base
<222> LOCATION: (17)..(17)
<223> OTHER INFORMATION: phosphorodithioate phosphate and fluoride sugar
      modification

<400> SEQUENCE: 48
ttacuguacg gcuagaugua c                                              21

<210> SEQ ID NO 49
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: monothiophosphate and fluoride sugar
      modification

<400> SEQUENCE: 49
ugacaugccg aucuacaugt t                                              21

<210> SEQ ID NO 50
<211> LENGTH: 21
<212> TYPE: DNA
```

```
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: monothiophosphate and fluoride sugar
      modification
<220> FEATURE:
<221> NAME/KEY: modified_base
<222> LOCATION: (12)..(12)
<223> OTHER INFORMATION: monothiophosphate and fluoride sugar
      modification

<400> SEQUENCE: 50
ugacaugccg aucuacaugt t                                                 21

<210> SEQ ID NO 51
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: monothiophosphate and fluoride sugar
      modification

<400> SEQUENCE: 51
ttacuguacg gcuagaugua c                                                 21

<210> SEQ ID NO 52
<211> LENGTH: 21
<212> TYPE: DNA
<213> ORGANISM: Artificial Sequence
<220> FEATURE:
<223> OTHER INFORMATION: siRNa
<220> FEATURE:
<221> NAME/KEY: modified_base
<222> LOCATION: (13)..(13)
<223> OTHER INFORMATION: monothiophosphate and fluoride sugar
      modification
<220> FEATURE:
<221> NAME/KEY: modified_base
<222> LOCATION: (17)..(17)
<223> OTHER INFORMATION: monothiophosphate and fluoride sugar
      modification

<400> SEQUENCE: 52
ttacuguacg gcuagaugua c                                                 21

<210> SEQ ID NO 53
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: fluoride sugar modification

<400> SEQUENCE: 53
ugacaugccg aucuacaugt t                                                 21

<210> SEQ ID NO 54
<211> LENGTH: 21
<212> TYPE: DNA
<213> ORGANISM: Artificial Sequence
<220> FEATURE:
```

```
<223> OTHER INFORMATION: siRNA
<220> FEATURE:
<221> NAME/KEY: modified_base
<222> LOCATION: (3)..(3)
<223> OTHER INFORMATION: fluoride sugar modification
<220> FEATURE:
<221> NAME/KEY: modified_base
<222> LOCATION: (12)..(12)
<223> OTHER INFORMATION: fluoride sugar modification

<400> SEQUENCE: 54
ugacaugccg aucuacaugt t                                            21

<210> SEQ ID NO 55
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (10)..(11)
<223> OTHER INFORMATION: fluoride sugar modification

<400> SEQUENCE: 55
ttacuguacg gcuagaugua c                                            21

<210> SEQ ID NO 56
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (13)..(13)
<223> OTHER INFORMATION: fluoride sugar modification
<220> FEATURE:
<221> NAME/KEY: modified_base
<222> LOCATION: (17)..(17)
<223> OTHER INFORMATION: fluoride sugar modification

<400> SEQUENCE: 56
ttacuguacg gcuagaugua c                                            21

<210> SEQ ID NO 57
<211> LENGTH: 82
<212> TYPE: DNA
<213> ORGANISM: Homo sapiens

<400> SEQUENCE: 57
caaagggtgg gacctgatgc agaacatcat gaatgacatg ccgatctaca tgtactccgt    60
gtgcaacgtg atgtctggcg ac                                            82

<210> SEQ ID NO 58
<211> LENGTH: 65
<212> TYPE: DNA
<213> ORGANISM: Artificial Sequence
<220> FEATURE:
<223> OTHER INFORMATION: EphA2 test target

<400> SEQUENCE: 58
acctgatgca gaacatcatg aacatgtaga tcggcatgtc atactccgtg tgcaacgtga    60
tgtct                                                                65

<210> SEQ ID NO 59
<211> LENGTH: 22
```

```
<212> TYPE: DNA
<213> ORGANISM: Artificial Sequence
<220> FEATURE:
<223> OTHER INFORMATION: siRNA

<400> SEQUENCE: 59
auacaggcag caguaacuuu tt                                              22

<210> SEQ ID NO 60
<211> LENGTH: 22
<212> TYPE: DNA
<213> ORGANISM: Artificial Sequence
<220> FEATURE:
<223> OTHER INFORMATION: siRNA

<400> SEQUENCE: 60
ttuauguccg ucgucauuga aa                                              22

<210> SEQ ID NO 61
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (19)..(20)
<223> OTHER INFORMATION: MePS2 (phosphorodithioate phosphate and methyl
      sugar) modification

<400> SEQUENCE: 61
auacaggcag caguaacuuu tt                                              22

<210> SEQ ID NO 62
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (5)..(5)
<223> OTHER INFORMATION: MePS2 (phosphorodithioate phosphate and methyl
      sugar) modification
<220> FEATURE:
<221> NAME/KEY: modified_base
<222> LOCATION: (10)..(10)
<223> OTHER INFORMATION: MePS2 (phosphorodithioate phosphate and methyl
      sugar) modification
<220> FEATURE:
<221> NAME/KEY: modified_base
<222> LOCATION: (15)..(15)
<223> OTHER INFORMATION: MePS2 (phosphorodithioate phosphate and methyl
      sugar) modification
<220> FEATURE:
<221> NAME/KEY: modified_base
<222> LOCATION: (20)..(20)
<223> OTHER INFORMATION: MePS2 (phosphorodithioate phosphate and methyl
      sugar) modification

<400> SEQUENCE: 62
auacaggcag caguaacuuu tt                                              22

<210> SEQ ID NO 63
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
```

```
<222> LOCATION: (19)..(20)
<223> OTHER INFORMATION: MePS2 (phosphorodithioate phosphate and methyl
      sugar) modification

<400> SEQUENCE: 63
ttuauguccg ucgucauuga aa                                              22

<210> SEQ ID NO 64
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: MePS2 (phosphorodithioate phosphate and methyl
      sugar) modification
<220> FEATURE:
<221> NAME/KEY: modified_base
<222> LOCATION: (12)..(12)
<223> OTHER INFORMATION: MePS2 (phosphorodithioate phosphate and methyl
      sugar) modification

<400> SEQUENCE: 64
auacaggcag caguaacuuu tt                                              22

<210> SEQ ID NO 65
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (14)..(14)
<223> OTHER INFORMATION: MePS2 (phosphorodithioate phosphate and methyl
      sugar) modification

<400> SEQUENCE: 65
ttuauguccg ucgucauuga aa                                              22

<210> SEQ ID NO 66
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (11)..(12)
<223> OTHER INFORMATION: MePS2 (phosphorodithioate phosphate and methyl
      sugar) modification

<400> SEQUENCE: 66
ttuauguccg ucgucauuga aa                                              22

<210> SEQ ID NO 67
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: MePS2 (phosphorodithioate phosphate and methyl
      sugar) modification

<400> SEQUENCE: 67
```
ugacaugccg aucuacaugt t                                              21

<210> SEQ ID NO 68
<211> LENGTH: 21
<212> TYPE: DNA
<213> ORGANISM: Artificial Sequence
<220> FEATURE:
<223> OTHER INFORMATION: siRNA

<400> SEQUENCE: 68
ttacuguacg gcuagaugua c                                              21

<210> SEQ ID NO 69
<211> LENGTH: 21
<212> TYPE: DNA
<213> ORGANISM: Artificial Sequence
<220> FEATURE:
<223> OTHER INFORMATION: siRNA

<400> SEQUENCE: 69
ugacaugccg aucuacaugt t                                              21

<210> SEQ ID NO 70
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: MePS (monothiophosphate and methyl sugar)
      modification

<400> SEQUENCE: 70
ugacaugccg aucuacaugt t                                              21

<210> SEQ ID NO 71
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: Phosphorodithioate modification

<400> SEQUENCE: 71
ugacaugccg aucuacaugt t                                              21

<210> SEQ ID NO 72
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: monothiophosphate (PS) modification

<400> SEQUENCE: 72
ugacaugccg aucuacaugt t                                              21

<210> SEQ ID NO 73
<211> LENGTH: 12
<212> TYPE: RNA

```
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: Phosphorodithioate modification

<400> SEQUENCE: 73
cgcgaauuag cg                                                             12

<210> SEQ ID NO 74
<211> LENGTH: 12
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (5)..(5)
<223> OTHER INFORMATION: MePS2 (phosphorodithioate phosphate and methyl
      sugar) modification

<400> SEQUENCE: 74
cgcgaauuag cg                                                             12

<210> SEQ ID NO 75
<211> LENGTH: 12
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (9)..(9)
<223> OTHER INFORMATION: MePS2 (phosphorodithioate phosphate and methyl
      sugar) modification

<400> SEQUENCE: 75
cgcgaauuag cg                                                             12

<210> SEQ ID NO 76
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (18)..(19)
<223> OTHER INFORMATION: monothiophosphate (PS)

<400> SEQUENCE: 76
ugacaugccg aucuacaugt t                                                   21

<210> SEQ ID NO 77
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: MePS2 (phosphorodithioate phosphate and methyl
      sugar) modification
<220> FEATURE:
<221> NAME/KEY: modified_base
<222> LOCATION: (14)..(14)
<223> OTHER INFORMATION: MePS2 (phosphorodithioate phosphate and methyl
      sugar) modification
```

```
<220> FEATURE:
<221> NAME/KEY: modified_base
<222> LOCATION: (16)..(16)
<223> OTHER INFORMATION: MePS2 (phosphorodithioate phosphate and methyl
      sugar) modification
<220> FEATURE:
<221> NAME/KEY: modified_base
<222> LOCATION: (18)..(18)
<223> OTHER INFORMATION: MePS2 (phosphorodithioate phosphate and methyl
      sugar) modification
<220> FEATURE:
<221> NAME/KEY: modified_base
<222> LOCATION: (19)..(19)
<223> OTHER INFORMATION: MePS2 (phosphorodithioate phosphate and methyl
      sugar) modification

<400> SEQUENCE: 77
ugacaugccg aucuacaugt t                                              21

<210> SEQ ID NO 78
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: MePS2 (phosphorodithioate phosphate and methyl
      sugar) modification
<220> FEATURE:
<221> NAME/KEY: modified_base
<222> LOCATION: (8)..(8)
<223> OTHER INFORMATION: MePS2 (phosphorodithioate phosphate and methyl
      sugar) modification

<400> SEQUENCE: 78
ttacuguacg gcuagaugua c                                              21

<210> SEQ ID NO 79
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (3)..(3)
<223> OTHER INFORMATION: MePS2 (phosphorodithioate phosphate and methyl
      sugar) modification

<400> SEQUENCE: 79
ttacuguacg gcuagaugua c                                              21

<210> SEQ ID NO 80
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: MePS2 (phosphorodithioate phosphate and methyl
      sugar) modification
<220> FEATURE:
<221> NAME/KEY: modified_base
<222> LOCATION: (14)..(14)
<223> OTHER INFORMATION: MePS2 (phosphorodithioate phosphate and methyl
      sugar) modification
<220> FEATURE:
<221> NAME/KEY: modified_base
<222> LOCATION: (18)..(19)
```

```
<223> OTHER INFORMATION: MePS2 (phosphorodithioate phosphate and methyl
      sugar) modification

<400> SEQUENCE: 80
ugacaugccg aucuacaugt t                                              21

<210> SEQ ID NO 81
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: modified_base
<222> LOCATION: (4)..(4)
<223> OTHER INFORMATION: MePS2 (phosphorodithioate phosphate and methyl
      sugar) modification
<220> FEATURE:
<221> NAME/KEY: modified_base
<222> LOCATION: (18)..(19)
<223> OTHER INFORMATION: MePS2 (phosphorodithioate phosphate and methyl
      sugar) modification

<400> SEQUENCE: 81
ugacaugccg aucuacaugt t                                              21
```

METHODS AND COMPOSITIONS OF IMPROVED MODIFIED SIRNA

CROSS REFERENCE TO RELATED APPLICATIONS

This application claims priority based on U.S. Provisional Application Ser. No. 61/951,518 filed Mar. 11, 2014, which is incorporated herein by reference.

STATEMENT REGARDING GOVERNMENT INTERESTS

This invention was made with government support under SBIR R44GM086937 awarded by the National Institutes of Health. The Government has certain rights in the invention.

REFERENCE TO SEQUENCE LISTING SUBMITTED ELECTRONICALLY

The Sequence Listing associated with the application is provided in text format in lieu of a paper copy, and is hereby incorporated by reference into the specification. The name of the text file containing the Sequence Listing is SequenceListing_ST25.txt. The text file is 24 kilobytes, was created on May 21, 2015, and is being submitted electronically via EFS-Web.

FIELD OF THE INVENTION

This invention relates generally to compositions and methods for improving siRNA based therapies.

BACKGROUND OF THE INVENTION

Without limiting the scope of the invention, its background is described in connection with existing siRNA based therapies. SiRNA-based therapies have shown promise in recent clinical trials as anti-cancer agents. See Tabernero, J. et al. "First-in-humans trial of an RNA interference therapeutic targeting VEGF and KSP in cancer patients with liver involvement" *Cancer Discov.* 3, 406-417 (2013). This technology offers tremendous potential in silencing "non-druggable" targets that are not amenable to conventional therapeutics such as small molecules or monoclonal antibodies. However, the lack of stability and low potency at target sites following systemic administration remain the major obstacles to clinical translation of this therapy. See e.g. Pecot, C., et al. "RNA interference in the clinic: challenges and future directions" *Nat. Rev. Cancer* 11, 59-67 (2011).

To overcome these problems, efforts have been made to chemically modify the 2'-position of the ribose moiety (e.g. 2'-OMe or 2'-F) or phosphate backbone of the siRNA molecule (e.g. phosphoromonothioate (PS) modification) such that enhanced serum stability, bioavailability, and prolonged duration of action could be achieved. See e.g. Behlke, M. A. "Progress towards in vivo use of siRNAs" *Mol. Ther.* 13, 644-670 (2006). Importantly, combining PS and 2'-modification impart superior stability over single modifications leading to the approval of Kynamro, an antisense therapeutic, by the Food and Drug Administration. See Stein, D., et al. "A specificity comparison of four antisense types: morpholino, 2'-O-methyl RNA, DNA, and phosphorothioate DNA" *Antisense Nucleic Acid Drug Dev.* 7, 151-157 (1997).

Despite the advance, the combination of PS and 2'-modification shows limited enhancement of siRNA potency. See e.g. Prakash, T. et al. "Positional effect of chemical modifications on short interference RNA activity in mammalian cells" *J. Med. Chem.* 48, 4247-4253 (2005).

From the foregoing it is apparent the there is a need in the art for improved strategies for the chemical modification of siRNAs such that their therapeutic potential can be realized.

SUMMARY OF THE INVENTION

Provide herein are chemically modified siRNA molecules including a combination of 2'-OMe and PS2 modifications on either or both sense and antisense strands that improve serum stability and gene silencing efficacy. In certain embodiments, both sense and antisense-strands of the siRNA contain dTdT on their 3' terminus. In other embodiments, a 3' end of the sense strand terminates in a sequence UGdTdT-3'. In certain embodiments, the 2'-OMe and PS2 modifications are in a backbone region adjacent to a 3'-dTdT overhang of the siRNA sense strand. In certain embodiments, a length of either the sense or antisense strand of the chemically modified siRNA is 21 nucleotides including a 3' dTdT sequence.

Also provided herein are chemically modified siRNAs directed against an RNA that generates a protein conferring chemo resistance wherein the chemical modifications comprise a combination of 2'-OMe and PS2 modifications on either or both sense and antisense strands that improve serum stability and gene silencing efficacy. Exemplified siRNAs include those directed to interference with the RISC Ago2 slicer associated with chemoresistance in ovarian cancer cell lines and tumors as well as chemically modified siRNAs directed to interference with GRAM Domain Containing 1B (GRAMD1B).

As disclosed herein, combination therapies for cancer chemotherapy were found particularly efficacious where a chemotherapeutic agent was delivered in the same course of treatment with a chemically modified siRNA that interferes with expression of a protein conferring resistance to the chemotherapeutic agent, wherein the chemical modifications to the siRNA comprise a combination of 2'-OMe and PS2 modifications on either or both sense and antisense strands of the siRNA that improve serum stability and gene silencing efficacy of the siRNA. Method of improving serum stability and gene silencing efficacy of the siRNAs are provided that include introducing a combination of 2'-OMe and PS2 modifications on either or both sense and antisense strands of the siRNA (sometimes referred to herein as MePS2 modifications) and testing for improved serum stability and gene silencing efficacy of the siRNA.

BRIEF DESCRIPTION OF THE DRAWINGS

For a more complete understanding of the present invention, including features and advantages, reference is now made to the detailed description of the invention along with the accompanying figures:

FIG. 2A shows the results of EphA2 protein quantification 48 h post-transfection with various modified siRNAs. MePS2-1, MePS2-2, Me-4, FPS-1, FPS-4, and F-1 significantly decreased EphA2 levels in SKOV3ip1 compared to unmodified (UM) siRNA and outperformed their counterparts.

FIG. 2B depicts the results of EphA2 protein quantification 48 h post-transfection with various modified siRNAs in HeyA8 cells. MePS2-1 modified siEphA2 also showed superior silencing activity compared to the UM sequence (80% vs. 50% knockdown, respectively.

FIG. 2H illustrates the chemical structures of further modified siRNAs with locations of modifications are indicated for each sequence.

FIG. 2I shows the results of knockdown of EphA2 in SKOV3ip1 cells using chemically modified siRNAs of FIG. 2H.

FIG. 3E shows that Interferon alpha (IFN-α) levels as a surrogate marker for non-specific induction of innate immunity, were similar for all four sequences examined.

FIG. 3F shows the efficacy of the MePS2-1 siRNA in vivo assessed using an orthotopic mouse model of ovarian cancer (SKOV3ip1).

FIG. 8 presents selected crystal data and refinement parameters for PS2 and MePS2 modified RNAs.

FIGS. 9A & B represents a cartoon of the expected mechanisms for improved siRNA function with the disclosed modifications.

DETAILED DESCRIPTION OF THE INVENTION

Figure 1A:
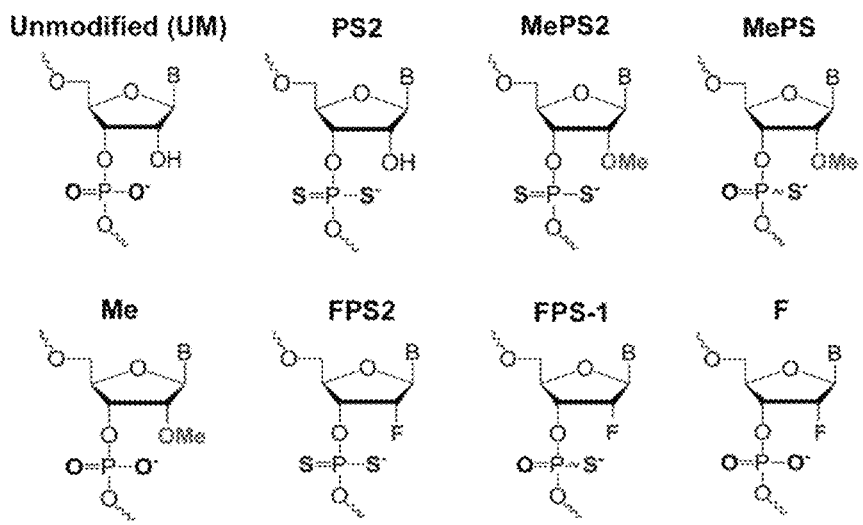
FIG. 1A illustrates structures of unmodified and modified ribonucleotides according to embodiments of the present invention.
Figure 1B:
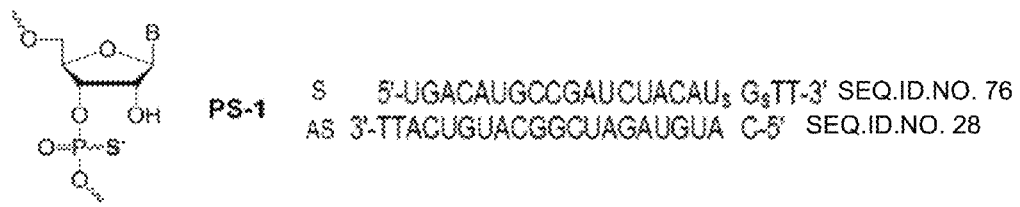
FIG. 1B represents the structure of the PS-1 modification and the sequence of the tested EPH receptor A2 (EphA2) siRNA with modification locations

The present inventor appreciated that, while the combination of PS and 2'-modifications to siRNA might be expected to solve stability problems that limited the therapeutic potential of siRNA, these modifications showed limited enhancement of siRNA potency. Furthermore, the present inventor appreciated that synthesis of PS or MePS by standard phosphoramidite methodology also generates a mixture of unresolvable diastereomeric oligomers, which could potentially result in variable biochemical, biophysical, and biological properties. The present inventor recently reported that PS2 modification, which substitutes sulfur atoms for both of the non-bridging phosphate and oxygen atoms, significantly improves serum stability and gene silencing over PS-modified siRNAs. Yang, X. et al. "Gene silencing activity of siRNA molecules containing phosphorodithioate substitutions" *ACS Chem. Biol.* 7, 1214-1220 (2012) 15. The achiral nature of PS2 modifications at the phosphorous center eliminates the generation of isomeric byproducts, thereby permitting batch to batch quality control, which is a feature that cannot be achieved with the MePS platform. See Wiesler, W. T. & Caruthers, M. H. "Synthesis of phosphorodithioate DNA via sulfur-linked, base-labile protecting groups" *J. Org. Chem.* 61, 4272-4281 (1996).

The solution described herein provides novel methods and compositions that introduce critical new features to PS2-modified siRNA thus further improving siRNA efficacy both in vitro and in vivo. The current inventor hypothesized that the incorporation of a sugar modification into a phosphorodithioate (PS2) modified construct could lead to further enhancement of the PS2 siRNA stability and increase its clinical potential. However, also important to the generation of these constructs was the placement of the modifications as will be later described. Two sugar modifications, 2'-O-Methyl (2'-OMe) and 2'-fluoride (2'-F) were tested. As demonstrated herein, the novel exemplified MePS2 design significantly enhances serum stability and silencing activity of siRNAs. This enhanced potency stems from an unforeseen increase in the loading of siRNAs to the RNA-induced silencing complex (RISC), likely due to the unique interaction mediated by 2'-OMe and PS2.

The therapeutic utility of MePS2-modified siRNAs is exemplified by targeting GRAM Domain Containing 1B (GRAMD1B). GRAMD1B is a novel gene identified through a whole genome taxane sensitivity screen and encodes a protein involved in chemoresistance. GRAMD1B silencing was achieved in tumors following MePS2-modified siRNA treatment, leading to a synergistic anti-tumor effect in combination with paclitaxel.

Given that limited success has been achieved thus far toward broadly enhancing siRNA potency with chemically modified siRNAs, the MePS2 modification provided herein represents a major new and unexpected direction for enhancing the clinical application of existing RNA interference (RNAi)-based therapies.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

ABBREVIATIONS

The following abbreviations are used throughout this application:
GRAMD1B GRAM Domain Containing 1B
PS2 phosphorodithioate
RISC RNA-induced silencing complex
siRNA small interfering RNA
UM unmodified To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Herein it is shown that novel dual modified siRNAs featuring 2'-X modification(s) of the ribose moiety on a backbone having a PS2 modification on the same base exhibit surprisingly improved siRNA silencing by a new mechanism. In one example, the siRNA chemistry provides MePS2 modified siRNAs selected with a whole genome lethality screen aimed at identifying novel genes involved in taxane resistance. This example demonstrates for the first time the feasibility of using highly potent MePS2 modified siRNAs for effective therapeutic targeting. Using GRAMD1B as a model system, it is demonstrated that robust gene silencing in tumors can be achieved following systemic administration of MePS2 modified siRNAs. This ultimately led to significant re-sensitization of chemoresistant ovarian tumors to taxane therapy.

Figure 6:
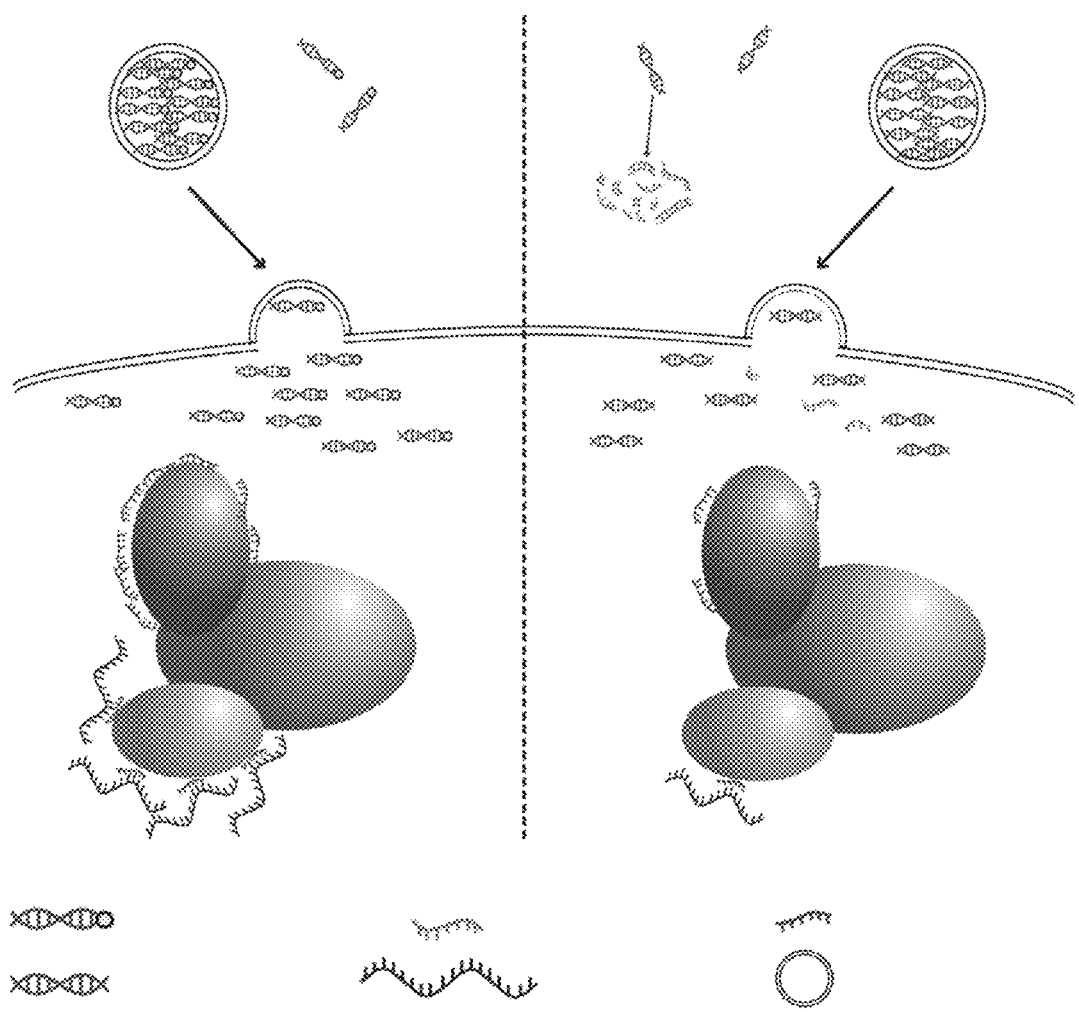
FIG. 6 represents a cartoon of the expected mechanisms for improved siRNA function with the disclosed modifications.

Most of the chemical modification strategies, to date, have focused on improving siRNA stability in serum. While this is critical, improving siRNA potency at target sites following systemic administration still remains the major obstacle to clinical translation of siRNAs as therapeutic modalities. Through a systematic approach, a unique combination of 2'-OMe and PS2 modifications (MePS2) was developed that significantly improves stability and potency of siRNAs simultaneously (FIG. 6). As shown herein, the increase in potency could not be explained by the design's enhanced stability, consistent with previous findings that this mechanism has a limited role within rapidly-dividing cells. In investigating other potential causes it was determined that, compared to PS2 modification, the exemplified MePS2 modification remarkably further enhances the loading of siRNAs to RISC resulting in enhanced silencing. While the addition of 2-O-methyl groups to RNA typically elevates Tm, here it is shown that the addition of 2'-OMe to PS2-modified siRNAs does not increase the Tm of the siRNA duplex, suggesting a unique property arising from this combination. Computational modeling also indicates an unusual favorable stereoelectronic effect on the siRNA backbone following MePS2 modification. These results indicate that certain modifications, including MePS2 modification, can improve the interaction of siRNA with RISC via several mechanisms, including potentially the thiol-protein interaction with the RISC complex, modulation of Tm, and altered stereoelectronics. This is in contrast to currently existing modifications, where RISC loading efficiency is dependent on alteration in Tm, thus leading to variable silencing effects depending on the Tm of the sequences to be modified. Hence, modifications, such as the exemplified MePS2 modification, have a unique potential to provide more consistent, sequence-independent, silencing effects compared to existing chemistries.

In the examples provided herein it is shown that a combination of 2'-OMe and PS2 modifications not only significantly increases the serum stability of siRNAs but also triggers a more potent intrinsic RNAi response than the individual modifications. In addition to its achiral nature, which favors clinical translation, the ability of the MePS2 modification to overcome major obstacles of bringing siRNA therapeutics into the clinic is demonstrated. In addition the achiral PS2 allows direct sulfur-protein interaction from either of the phosphoryl sulfur atoms whereas in a diastereomeric mixture with a monothiophosphate only one half of the diasteromers will have the phosphoryl sulfur pointed to the corrected interaction with the protein, while the other diasteromer will have a phosphoryl oxygen pointed to the specific interaction with the RISC protein. In the latter case this diastereomer would exhibit much poorer binding, comparable to the UM form. If more than one PS2 group were to be replaced by monothiophosphates, then even more of the diastereomeric mixture ($\frac{3}{4}^{th}$ for two modifications, $\frac{7}{8}$ths for three, etc.) would have improper phosphoryl oxygen-protein interactions thus highlighting the value of the PS2 group.

The following examples are included for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Locations of PS2 Modifications

Figure 1C:
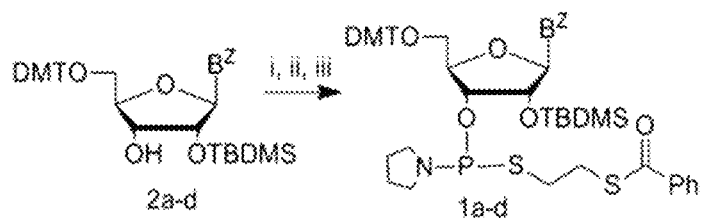
FIG. 1C depicts synthesis of certain thiophosphoramidites.
Figure 1D:
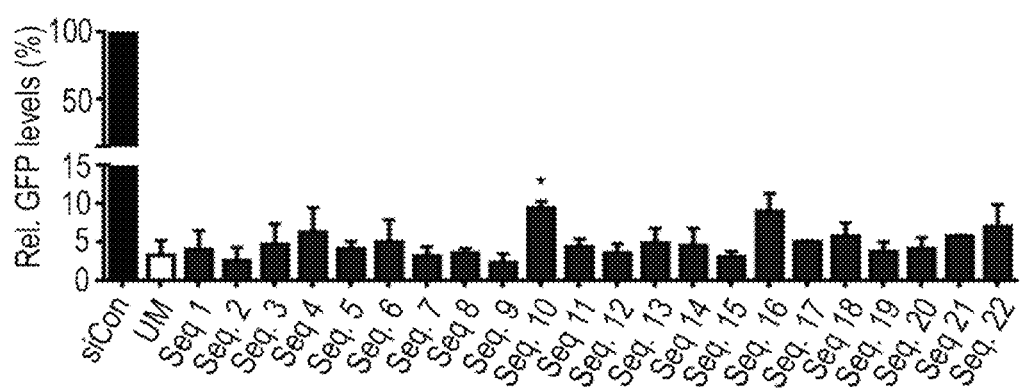
FIG. 1D depicts the results of silencing of Green fluorescence protein (GFP) by a panel of PS2-modified GFP-targeted siRNAs.

Favorable positions of PS2 modification were identified using an siRNA that targets Green Fluorescence Protein (GFP) as shown in Table 1. FIG. 1D shows the silencing efficiency of the PS2-modified siRNAs of FIG. 1D. In FIG. 1D, P-values were obtained with Student's t-test; *=P<0.05, compared to unmodified (UM) siGFP; bars and error bars represent mean values and the corresponding S.E.M.s (n=3).

TABLE 1

SiRNA sequences for a panel of PS2-modified siGFPs. Nucleotides underlined are modified with PS2 chemistry.

| No. | | SiRNA sequences | SEQ.ID. |
|---|---|---|---|
| Control | S | 5'-AAUCAGAUUGAACCUUCAUTT-3' | 1 |
| | AS | 3'-TTUUAGUCUAACUUGGAAGUA-5' | 2 |
| UM | S | 5'-ACAUGAAGCAGCACGACUUTT-3' | 3 |
| | AS | 3'-TTUGUACUUCGUCGUGCUGAA-5' | 4 |
| 1 | S | 5'-ACAUGAAGCAGCACGACU_U_TT-3' | 5 |
| | AS | 3'-TTUGUACUUCGUC_G_UGCUGAA-5' | |
| 2 | S | 5'-ACAUGAAGCAGCACGAC_U_UTT-3' | 6 |
| | AS | 3'-TTUGUACUUCGUCGUGCUGAA-5' | |
| 3 | S | 5'-ACAUGAAGCAGCACGACUUTT-3' | 7 |
| | AS | 3'-TTUGUACUUCGUCGUGCUG_A_A-5' | |
| 4 | S | 5'-ACAUGAAGCAGCACGACUUTT-3' | 8 |
| | AS | 3'-TTUGUACUUCGUCGUGCUG_A_A-5' | |
| 5 | S | 5'-AC_A_UGAAGC_A_GC_AC_GAC_U_UTT-3' | 9 |
| | AS | 3'-TTUGUACUUCGUC_G_UGCUGAA-5' | |
| 6 | S | 5'-_A_CAUGA_A_GCAG_A_CGACU_U_TT-3' | 10 |
| | AS | 3'-TTUGUACUUCGUC_G_UCUGAA-5' | |
| 7 | S | 5'-AC_A_UGAAGC_A_GCACGACU_U_TT-3' | 11 |
| | AS | 3'-TTUGUACUUCGUCGUGCUGAA-5' | |
| 8 | S | 5'-ACAUGAAGC_A_GCACGACU_U_TT-3' | 12 |
| | AS | 3'-TTUGUACUUCGUCGUGCUGAA-5' | |
| 9 | S | 5'-AC_A_UGAAGC_A_GCACGACUUTT-3' | 13 |
| | AS | 3'-TTUGUAC_U_UCGUCGUGCUGAA-5' | |
| 10 | S | 5'-ACAUGAAGCAGCACGACUUTT-3' | 14 |
| | AS | 3'-TT_U_GUACU_U_CGUCG_U_GCUG_A_A-5' | |
| 11 | S | 5'-ACAUGAAGCAGCACGACUUTT-3' | 15 |
| | AS | 3'-TTUG_U_ACUUCG_U_CGUGCUG_A_A-5' | |
| 12 | S | 5'-ACAUG_A_AGCACGACUUTT-3' | 16 |
| | AS | 3'-TT_U_GUACUUCGUCGUCG_A_A-5' | |
| 13 | S | 5'-ACAUGAAGCAGCACGACUUTT-3' | 17 |
| | AS | 3'-TTUGUACUUCG_U_CGUGCUGAA-5' | |
| 14 | S | 5'-ACAUGAAGCAGCACGACUUTT-3' | 18 |
| | AS | 3'-TTUGUAC_U_UCG_U_CGUGCUGAA-5' | |
| 15 | S | 5'-ACAUGAAGCAGCACGACUUTT-3' | 19 |
| | AS | 3'-TTUGUACUUC_G_UCGUGCUGAA-5' | |
| 16 | S | 5'-ACAUGAAGCAGCACGACUUTT-3' | 20 |
| | AS | 3'-TTUGUACUUCGUC_G_UGCUGAA-5' | |
| 17 | S | 5'-ACAUGAAGCAGCACGACUUTT-3' | 21 |
| | AS | 3'-TTUGUACUUCGUCGUC_U_GAA-5' | |
| 18 | S | 5'-ACAUGAAGCAGCACGACUUTT-3' | 22 |
| | AS | 3'-TTUGUACUUCGUC_G_UGCUGAA-5' | |
| 19 | S | 5'-ACAUGAAGCAGCACGACUUTT-3' | 23 |
| | AS | 3'-TT_U_GUACUUC_G_UCGUGCUGAA-5' | |
| 20 | S | 5'-ACAUGAAGCAGCACGACUUTT-3' | 24 |
| | AS | 3'-TT_U_GUACU_U_CGUCGUGCUGAA-5' | |
| 21 | S | 5'-ACAUGAAGCAGCACGACUUTT-3' | 25 |
| | AS | 3'-TT_U_GUACUUCGUCGUGCUGAA-5' | |
| 22 | S | 5'-ACAUGAAGCAGCACGACUUTT-3' | 26 |
| | AS | 3'-TTUGU_A_CUUCGUCGUGCUGAA-5' | |

The silencing efficacy of selected PS2-modified sequences was further validated using another siRNA sequence. See Yang, X. et al. "Gene silencing activity of siRNA molecules containing phosphorodithioate substitutions" *ACS Chem. Biol.* 7, 1214-1220 (2012).

EXAMPLE 2

Synthesis and Activity of Chemically Modified siRNAs

To investigate the gene silencing activity of MePS2- or FPS2-siRNAs and to gain insight into their regulation of the RNAi pathway, the novel siRNAs were first synthesized via the solid-phase synthesis technique. EPH receptor A2 (EphA2), a tyrosine kinase receptor that promotes tumor progression in cancer, was initially chosen to evaluate the novel MePS2 modified siRNAs using EphA2 as a model system. Informed by observations with the GFP system, MePS2/FPS2-1 through -3 constructs for siEphA2 (FIG. 1A, Table 2) were designed. MePS2/FPS2-4 sequences were also created having two MePS2/FPS2 groups present at the seed region of the antisense strand. Lastly, counterpart sequences were synthesized with either 2'-OMe/2'-F alone, PS2 alone, or MePS/FPS placed at the same locations.

TABLE 2

Chemical structures of modified siRNAs. Chemical structures of modified sense (S) and antisense (AS) siRNAs used for the initial screen. Locations of modification are indicated for each sequence.

| | Sense (5' to 3') | Antisense (3' to 5') |
|---|---|---|
| UM | UGACAUGCCGAUCUACAUGTT SEQ.ID.NO. 27 | TTACUGUACGGCUAGAUGUAC SEQ.ID.NO. 28 |
| PS2-1 | UGACAUGCCGAUCUACAU$_{S2}$G$_{S2}$TT SEQ.ID.NO. 29 | TTACUGUACGGCUAGAUGUAC |
| PS2-2 | UGA$_{S2}$CAUGCCGAU$_{S2}$CUACAUGTT SEQ.ID.NO. 30 | TTACUGUACGGCUAGAUGUAC |
| PS2-3 | UGACAUGCCGAUCUACAUGTT | TTACUGUACG$_{S2}$G$_{S2}$CUAGAUGUAC SEQ.ID.NO. 31 |

TABLE 2-continued

Chemical structures of modified siRNAs.
Chemical structures of modified sense (S) and antisense (AS)
siRNAs used for the initial screen. Locations of modification
are indicated for each sequence.

| | Sense (5' to 3') | Antisense (3' to 5') |
|---|---|---|
| PS2-4 | UGACAUGCCGAUCUACAUGTT | TTACUGUACGGCU$_{S2}$AGAU$_{S2}$GUAC SEQ.ID.NO. 32 |
| MePS2-1 | UGACAUGCCGAUCUACAU$_{MeS2}$G$_{MeS2}$TT SEQ.ID.NO. 33 | TTACUGUACGGCUAGAUGUAC |
| MePS2-2 | UGA$_{MeS2}$CAUGCCGAU$_{MeS2}$CUACAUGTT SEQ.ID.NO. 34 | TTACUGUACGGCUAGAUGUAC |
| MePS2-3 | UGACAUGCCGAUCUACAUGTT | TTACUGUACG$_{MeS2}$G$_{MeS2}$CUAGAUGUAC SEQ.ID.NO. 35 |
| MePS2-4 | UGACAUGCCGAUCUACAUGTT | TTACUGUACGGCU$_{MeS2}$AGAU$_{MeS2}$GUAC SEQ.ID.NO. 36 |
| MePS-1 | UGACAUGCCGAUCUACAU$_{MeS}$G$_{MeS}$TT SEQ.ID.NO. 37 | TTACUGUACGGCUAGAUGUAC |
| MePS-2 | UGA$_{MeS}$CAUGCCGAU$_{MeS}$CUACAUGTT SEQ.ID.NO. 38 | TTACUGUACGGCUAGAUGUAC |
| MePS-3 | UGACAUGCCGAUCUACAUGTT | TTACUGUACG$_{MeS}$G$_{MeS}$CUAGAUGUAC SEQ.ID.NO. 39 |
| MePS-4 | UGACAUGCCGAUCUACAUGTT | TTACUGUACGGCU$_{MeS}$AGAU$_{MeS}$GUAC SEQ.ID.NO. 40 |
| Me-1 | UGACAUGCCGAUCUACAU$_{Me}$G$_{Me}$TT SEQ.ID.NO. 41 | TTACUGUACGGCUAGAUGUAC |
| Me-2 | UGA$_{Me}$CAUGCCGAU$_{Me}$CUACAUGTT SEQ.ID.NO. 42 | TTACUGUACGGCUAGAUGUAC |
| Me-3 | UGACAUGCCGAUCUACAUGTT | TTACUGUACG$_{Me}$G$_{Me}$CUAGAUGUAC SEQ.ID.NO. 43 |
| Me-4 | UGACAUGCCGAUCUACAUGTT | TTACUGUACGGCU$_{Me}$AGAU$_{Me}$GUAC SEQ.ID.NO. 44 |
| FPS2-1 | UGACAUGCCGAUCUACAU$_{FS2}$G$_{FS2}$TT SEQ.ID.NO. 45 | TTACUGUACGGCUAGAUGUAC |
| FPS2-2 | UGA$_{FS2}$CAUGCCGAU$_{FS2}$CUACAUGTT SEQ.ID.NO. 46 | TTACUGUACGGCUAGAUGUAC |
| FPS2-3 | UGACAUGCCGAUCUACAUGTT | TTACUGUACG$_{FS2}$G$_{FS2}$CUAGAUGUAC SEQ.ID.NO. 47 |
| FPS2-4 | UGACAUGCCGAUCUACAUGTT | TTACUGUACGGCU$_{FS2}$AGAU$_{FS2}$GUAC SEQ.ID.NO. 48 |
| FPS-1 | UGACAUGCCGAUCUACAU$_{FS}$G$_{FS}$TT SEQ.ID.NO. 49 | TTACUGUACGGCUAGAUGUAC |
| FPS-2 | UGA$_{FS}$CAUGCCGAU$_{FS}$CUACAUGTT SEQ.ID.NO. 50 | TTACUGUACGGCUAGAUGUAC |
| FPS-3 | UGACAUGCCGAUCUACAUGTT | TTACUGUACG$_{FS}$G$_{FS}$CUAGAUGUAC SEQ.ID.NO. 51 |
| FPS-4 | UGACAUGCCGAUCUACAUGTT | TTACUGUACGGCU$_{FS}$AGAU$_{FS}$GUAC SEQ.ID.NO. 52 |
| F-1 | UGACAUGCCGAUCUACAU$_{F}$G$_{F}$TT SEQ.ID.NO. 53 | TTACUGUACGGCUAGAUGUAC |
| F-2 | UGA$_{F}$CAUGCCGAU$_{F}$CUACAUGTT SEQ.ID.NO. 54 | TTACUGUACGGCUAGAUGUAC |
| F-3 | UGACAUGCCGAUCUACAUGTT | TTACUGUACG$_{F}$G$_{F}$CUAGAUGUAC SEQ.ID.NO. 55 |

TABLE 2-continued

Chemical structures of modified siRNAs.
Chemical structures of modified sense (S) and antisense (AS)
siRNAs used for the initial screen. Locations of modification
are indicated for each sequence.

| | Sense (5' to 3') | Antisense (3' to 5') |
|---|---|---|
| F-4 | UGACAUGCCGAUCUACAUGTT | TTACUGUACGGCU$_F$AGAU$_F$GUAC<br>SEQ.ID.NO. 56 |

SKOV3ip1 and HeyA8, both epithelial ovarian cancer cell lines that highly express EphA2, were transfected with synthesized siRNAs in serum-free conditions to test silencing efficacy. Two independent experiments were performed and EphA2 protein quantification was done at 48 h post-transfection. MePS2-1, MePS2-2, Me-4, FPS-1, FPS-4, and F-1 significantly decreased EphA2 levels in SKOV3ip1 compared to unmodified (UM) siRNA and outperformed their counterparts (FIG. 2A). In particular, it was found that the MePS2-1 modification silenced EphA2 to a much greater degree compared to UM (6-fold enhancement). It also showed 4, 7.5, and 7-fold enhancement in EphA2 silencing compared to PS2-1, MePS-1, and Me-1 modified sequences, respectively. In contrast to MePS2-1 and MePS2-2, FPS2-1 and FPS-2 modifications did not increase silencing efficiency of the siRNA. Given the significant improvement in gene silencing observed with MePS2-1, subsequent efforts were focused on Me-modified constructs. In HeyA8 cells, MePS2-1 modified siEphA2 also showed superior silencing activity compared to the UM sequence (80% vs. 50% knockdown, respectively, FIG. 2B). Interestingly, both PS2-1 and PS2-2 modified sequences resulted in significant silencing of EphA2 in this cell line.

Figure 2C:
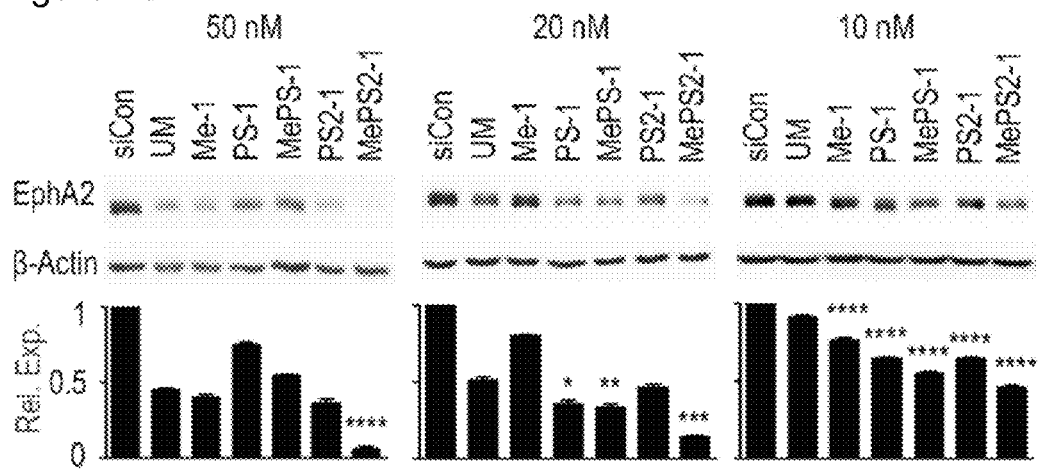
FIG. 2C shows the impact of different modifications at the same position on gene silencing EphA2 protein levels examined 48 h post-transfection.
Figure 2D:
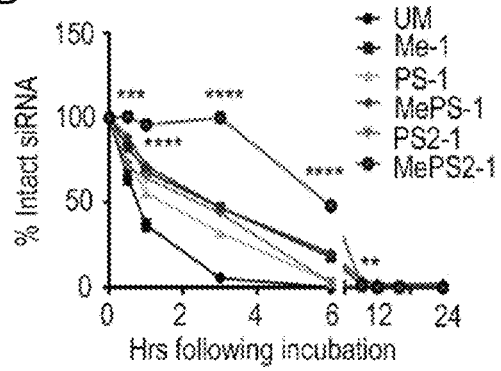
FIG. 2D shows the serum stability impact of the various modifications on the EphA2 siRNA.
Figure 2E:
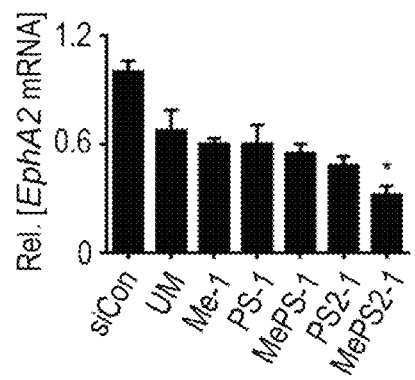
FIG. 2E shows EphA2 protein levels examined 24 h post-transfection with a panel of modifications of the same siRNA sequence. MePS2-1 displayed a significant improvement over all other sequences tested, including PS2-1.

Given the promise of the MePS2-1 modification in both of the cell lines examined, the impact of different modifications at the same position on gene silencing and serum stability (FIG. 2C, D) was next investigated. To mimic the condition in the pre-clinical or clinical setting, sequences were introduced into SKOV3ip1 cells in media containing 10% Fetal Bovine Serum (FBS). EphA2 protein levels were examined 48 h post-transfection. MePS2-1 displayed a significant improvement over all other sequences tested, including PS2-1 (FIG. 2C and FIG. 2E). For the data presented in FIG. 2E, EphA2 mRNA levels were assessed at 24 h post-transfection. Transfection was performed at 50 nM in SKOV3ip1 cells in the presence of 10% FBS. [P-value obtained with Student's t-test; *, P<0.05, compared to UM siEphA2; bars and error bars represent mean values and the corresponding S.E.M.s (n=3)].

The improved gene-silencing as the result of MePS2-1 modification was also observed when another siRNA sequence was used [parathymosin (PTMS) targeted siRNA, data not shown]. SiRNA stability assays show that the majority of UM siRNA was broken down within 20 min, with near-complete degradation at 3 h (FIG. 2D). Overall improvements in serum stability were seen for all modified sequences in comparison to UM, but MePS2-1 displayed the highest sequence stability, with a large portion of the input molecules remaining intact at 3 h. An even greater enhancement in stability was observed with PTMS-targeted siRNA (data not shown).

Figure 2F:
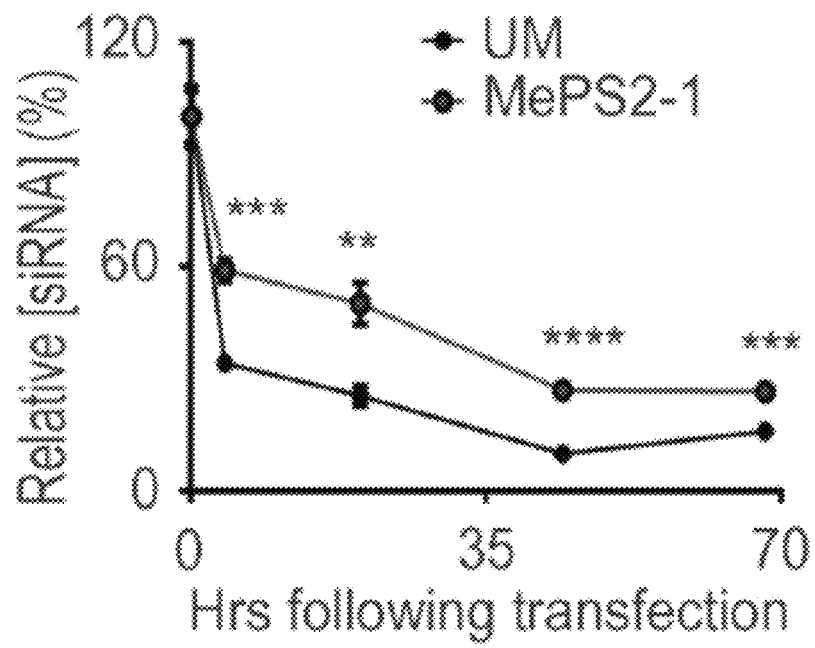
FIG. 2F illustrates the results of stem loop polymerase chain reaction (PCR) to quantify intact siRNA within the cell following transfection.
Figure 2G:
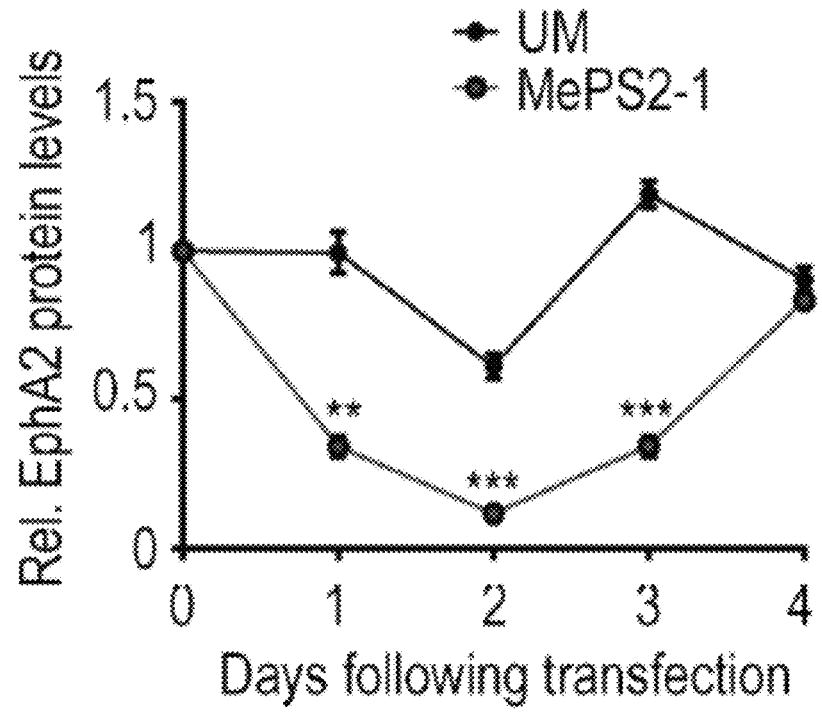
FIG. 2G illustrates that the duration of silencing was not significantly prolonged for MePS2-1 sequence compared to the UM counterpart.

It was next investigated whether the enhanced stability after modification accounted for these constructs' increased silencing efficacy. To test this, stem loop polymerase chain reaction (PCR) technique was employed to quantify intact siRNA within the cell following transfection (FIG. 2F). Increased intracellular siRNA stability via MePS2 modification was confirmed, but not to a degree that would explain its dramatic increase in siRNA potency. It was concluded that MePS2-1 showed increased potency independent of improvements in stability. This was consistent with the finding that the duration of silencing was not significantly prolonged for MePS2-1 sequence compared to the UM counterpart (FIG. 2G).

Of note, further modifications at different positions of the MePS2-1 siEphA2 sequence resulted in reduced silencing efficiency (FIG. 2H, I). FIG. 2H shows chemical structures of modified siRNAs with the locations of modification indicated for each sequence. FIG. 2I depicts knockdown of EphA2 in SKOV3ip1 cells using the chemically modified siRNAs of FIG. 2H (50 nM, 10% FBS containing media). [P-values obtained with Student's t-test; , P<0.01; *, P<0.001; ****, P<0.0001; compared to UM siEphA2; bars and error bars represent mean values and the corresponding S.E.M.s (n=3)].

EXAMPLE 3

Biophysical Properties of MePS2-1 siRNA

The mechanism by which the MePS2-1 sequence enhances the gene silencing effect was next examined. First, the thermodynamic stability [measured by RNA duplex melting temperature (Tm)] was examined since the destabilization of the 5'-end of duplex by introducing modified units into 3'-end of the sense strand is important in creating favorable thermodynamic asymmetry for siRNA activity. Measuring the Tm of MePS2-1 and its counterpart sequences showed MePS2-1 to have the largest decrease in Tm (1.24° C., $\Delta$Tm, P<0.05) when compared to UM siRNA, suggesting duplex unwinding may have a role in its enhanced RNAi activity (Table 3). Importantly, in contrast to 2'-OMe modification alone which increased Tm, its addition at the site of PS2 modification did not elevate Tm.

TABLE 3

Thermostability of chemically modified siRNAs

| siRNA<br>sequence | Average Tm<br>(° C.) | Std. Dev. (° C.) | $\Delta$Tm (° C.) |
|---|---|---|---|
| UM | 76.51 | 0.64 | N/A |
| Me-1 | 76.68 | 0.50 | 0.17 |
| PS-1 | 75.91 | 0.65 | −0.60 |
| MePS-1 | 76.37 | 0.08 | −0.14 |
| PS2-1 | 75.82 | 0.50 | −0.69 |
| MePS2-1 | 75.27 | 0.07 | −1.24 |

Figure 3A:
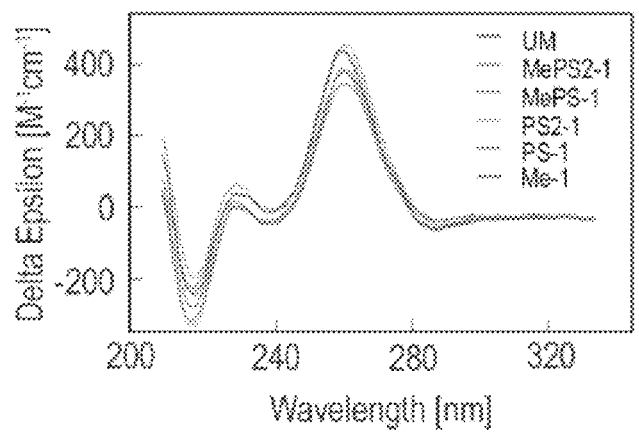
FIG. 3A shows that the circular dichroism (CD) spectra of all the modified sequences tested were similar to the spectrum of UM duplexes and are consistent with the typical A-type.

Investigations were made into whether the MePS2 modification altered helix conformation between the target and guide strand by changing local structure, which can affect silencing activity. However, circular dichroism (CD) spectra of all the modified sequences tested were similar to the spectrum of UM duplexes and are consistent with the typical A-type structure (a maximum of the positive Cotton effect at 268 nm and a crossover point at 240 nm) (FIG. 3A).

Figure 3B:
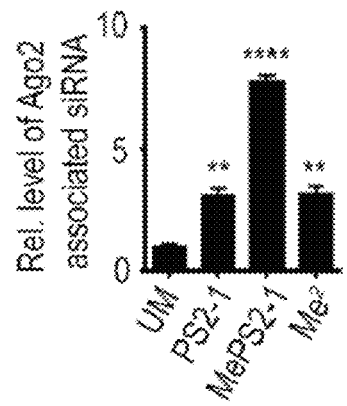
FIG. 3B shows the results of investigations into MePS2 group interactions with metal ions or amino acid residues in RISC by transfecting UM, PS2-1, and MePS2-1 into SKOV3ip1 cells, then immunoprecipitating argonaute-2 (Ago2). As shown, Ago2-associated MePS2-1 and PS2-1 sequences were enriched 7-fold and 3-fold compared to UM siRNA, respectively.
Figure 3C:
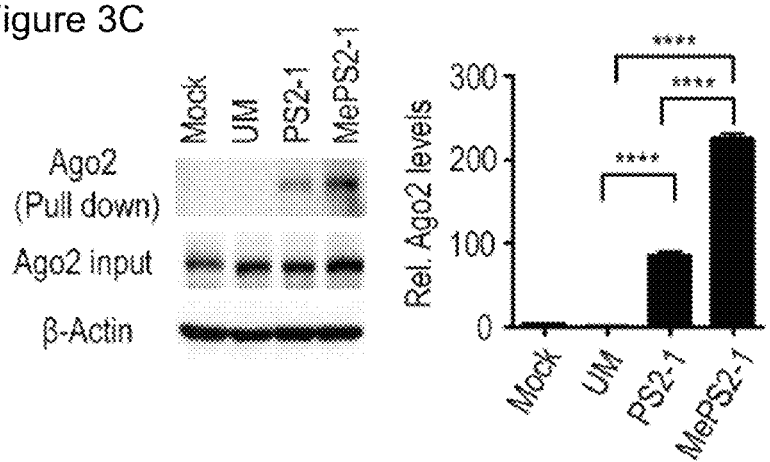
FIG. 3C shows that a high level of siRNA-associated Ago2 was detected for both PS2-1 and MePS2-1 siRNAs in the biotin-siRNA pull-down study.

Investigations were undertaken into whether the thiol groups on MePS2-1's phosphate backbone were interacting with metal ions or amino acid residues in RISC to increase the sequence's affinity for the complex. This hypothesis was tested by transfecting UM, PS2-1, and MePS2-1 into SKOV3ip1 cells, then immunoprecipitating argonaute-2 (Ago2). SiEphA2 with two 2'-OMe residues at the 5'-end of the sense strand (Me2-siEphA2) was used as a positive control. From a panel of 10 different microRNAs (miR) tested, hsa-miR-484 was found to be both unaffected by siEphA2 and present at a high level in SKOV3ip1 cells, thus it was chosen as a normalizing control. It was found that Ago2-associated MePS2-1 and PS2-1 sequences were enriched 7-fold and 3-fold compared to UM siRNA, respectively (FIG. 3B). In contrast to UM siRNA where the level of associated Ago2 protein was below the limit of detection via Western blotting, a high level of siRNA-associated Ago2 was detected for both PS2-1 and MePS2-1 siRNAs in the biotin-siRNA pull-down study (FIG. 3C). In both of these experiments, there was a significant increase in Ago2 binding for MePS2-1 compared to PS2-1 sequence (>2-fold). The ability of MePS2-1 modification to enhance loading of siRNAs into RISC was also demonstrated using another siRNA sequence (data not shown). Of note, the enhanced binding of MePS2-1 siRNAs to RISC had minimal effect on miR biogenesis.

The impact of MePS2-1 modification on strand loading was further investigated. SKOV3ip1 cells were transfected with siEphA2 sense (S) and antisense (AS) strand-specific luciferase reporters. MePS2-1(S) decreased the luciferase signal to a much greater degree (2.2-fold enhancement) compared to UM siRNA in cells transfected with the AS reporter construct. As expected, MePS2-1(AS) did not reduce the luciferase signal significantly when compared to control siRNA (siCon) treatment. Conversely, in cells transfected with the S reporter construct, MePS2-1(AS) further improved the silencing ability of the siRNAs when compared to the UM sequence, while no silencing was observed with MePS2-1(S).

The silencing efficacy of MePS2-1(S) was compared with Me2(S)-siRNA. In cells transfected with the AS reporter construct, Me2(S) siRNAs decreased the luciferase signal to a greater extent compared to UM, as expected. This extent of silencing was comparable to that achieved by MePS2-1 (S). The addition of MePS2-1(S) modification to Me2(S)-siRNA (Me2MePS2-1) did not significantly alter its silencing efficiency. These results are consistent with the level of EphA2 mRNA knockdown observed with these siRNAs.

Figure 3D:
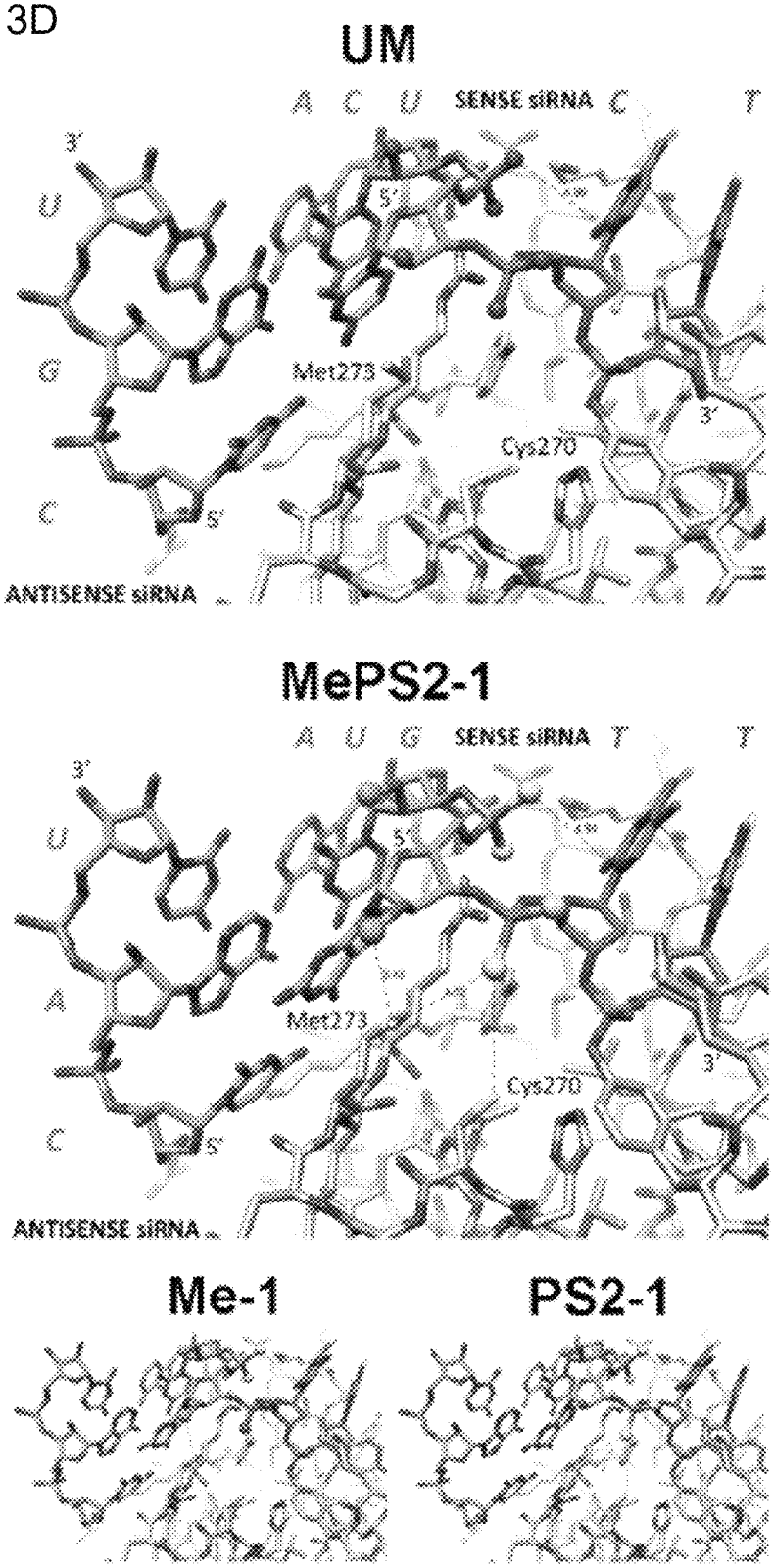
FIG. 3D illustrates computational models of MePS2-1 bound to PAZ indicating that the combination of the 2'-OMe and PS2 modifications will likely benefit the interaction between siRNA and PAZ.

Computational modeling was next used to examine the potential effects of the MePS2 modification on the interaction of siRNAs with RISC, focusing on the PAZ domain that recognizes 3'-overhanging nucleotides of siRNA duplexes. In the crystal structure, the siRNA 5'-(CGUGACU)-d(CU)-3' forms a duplex with one G-G and two U-C mismatch pairs and 3'-terminal d(CU) overhangs. Modeling entailed changing the penultimate 3'-dC to T, converting the terminal RNA U-C pair in the native duplex to G:C, and changing the adjacent G:C pair to A:U. Methyl groups were also added to the sugar 2'-oxygen atoms of U and G in the antiperiplanar orientation (torsion angle $C3'-C2'-O2'-C_{methyl}^{30}$). Inspection of the model of MePS2-1 bound to PAZ indicates that the combination of the 2'-OMe and PS2 modifications will likely benefit the interaction between siRNA and PAZ (FIG. 3D). Thus, the proximities of the 2'-OMe moiety of G and Cε of M273 as well as the PS2 moiety of T and both Cε of Met273 and the sulfhydryl group of C270 are consistent with favorable hydrophobic interactions that are absent in the complex with the UM siRNA and are superior to those for the Me-1 and PS2-1 siRNAs. Taken together, the combination of PS2 and 2'-OMe modification triggers an unusual stereoelectronic effect in the backbone of the siRNA, which leads to increased RISC loading. This, along with an increase in resistance to nuclease degradation as well as a decrease in Tm, provides a likely explanation for enhanced RNAi activity by MePS2-1 modification.

EXAMPLE 4

In Vivo Application of MePS2-1 siRNA

Having identified a promising chemical modification that could significantly enhance the stability and silencing activity of siRNAs, its potential off-target immunotoxicity was next characterized. C57BL/6-derived dendritic cells were treated with UM control siRNA (siCon), UM siEphA2, MePS2-1 siCon, and MePS2-1 siEphA2. Interferon alpha (IFN-α) levels, a surrogate marker for non-specific induction of innate immunity, were similar for all four sequences examined (FIG. 3E). No difference in Toll like receptor 7 (TLR7)-induced IFN-α or tumor necrosis factor alpha (TNF-α) levels was observed between UM siEphA2 and MePS2-1 siEphA2 at all time-points examined. Of note, serum IFN-α and TNF-α levels were both undetectable at 2, 6, and 24 h following intraperitoneal (i.p.) administration of 1,2-dioleoyl-sn-glycero-3-phosphatidylcholine (DOPC) nanoliposomes-delivered UM-siEphA2 (UM-siEphA2-DOPC) or MePS2-1 siEphA2 (MePS2-1-siEphA2-DOPC) in mice.

Figure 3I:
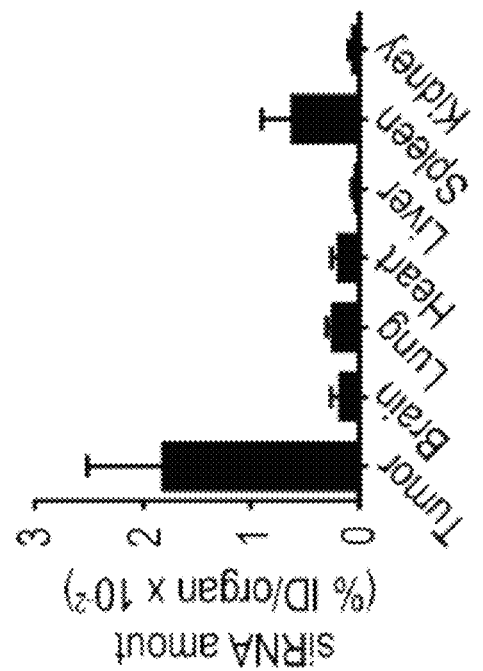
FIGS. 3G-I illustrate the effects of treatment of mice with 2.5 μg of UM-siCon-DOPC, UM-siEphA2-DOPC, MePS2-1-siCon-DOPC, and MePS2-1-siEphA2-DOPC twice weekly (n=10) and measurement of the tumor burden after four weeks of therapy.
Figure 3H:
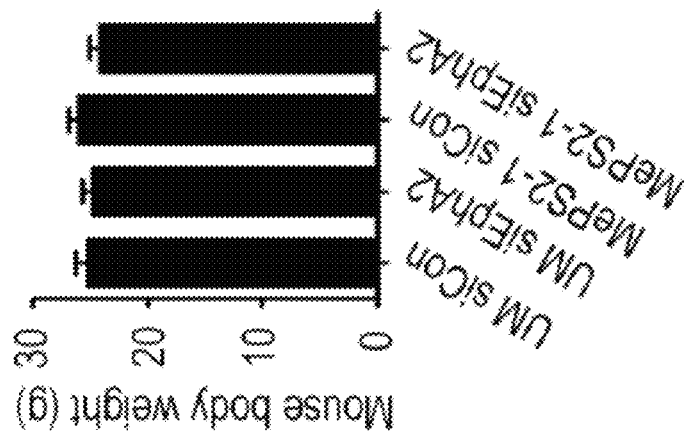
Figure 3G:
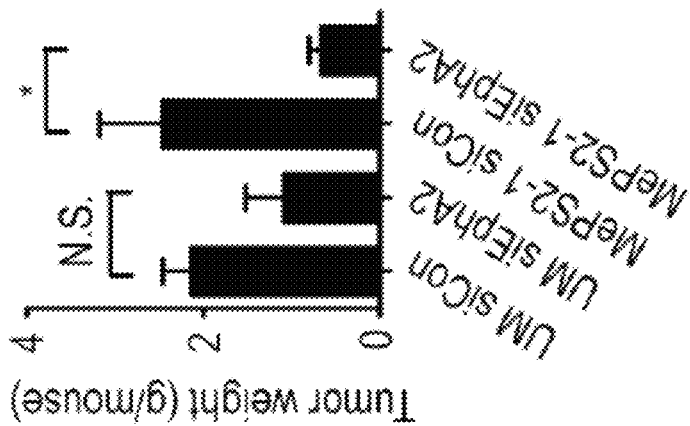

The efficacy of the MePS2-1 siRNA in vivo was next assessed using an orthotopic mouse model of ovarian cancer (SKOV3ip1). The effect of EphA2 knockdown in tumors was first examined following a single injection. While some degree of knockdown was achieved with MePS2-1-siEphA2-DOPC at the dose of 1.25 μg, (FIG. 3F), >2.5 μg per dose was determined to be necessary to achieve consistent and significant gene silencing in tumors. At the dose of 2.5 μg, measurement of EphA2 by Western blot of tumor lysate revealed superior gene silencing effect of MePS2-1-siEphA2-DOPC compared to UM-siEphA2-DOPC (80% vs. 30% reduction, respectively). Mice were next treated with 2.5 μg of UM-siCon-DOPC, UM-siEphA2-DOPC, MePS2-1-siCon-DOPC, and MePS2-1-siEphA2-DOPC twice weekly (n=10). After four weeks of therapy, the animals were sacrificed and necropsies were performed. UM-siEphA2-DOPC reduced the tumor burden compared to UM-siCon-DOPC group (50% reduction), however, the difference is not statistically significant. In contrast, MePS2-1-siEphA2-DOPC exhibited significant reduction in tumor weight (FIG. 3G, 70% reduction) compared to the MePS2-1-siCon-DOPC treatment group. No group showed decreased body weight, one major indicator of toxicity (FIG. 3H). Overall, these results demonstrate superior gene silencing and therapeutic effects with MePS2-1-siEphA2-DOPC compared to UM-siEphA2-DOPC.

The pharmacokinetic profile and biodistribution pattern of MePS2-1-siEphA2-DOPC was next evaluated following a single i.p. injection in tumor-bearing mice. The level of siRNAs accumulated in tumors was found to be significantly higher than that observed in other major organs, including lung, heart, liver, spleen, kidneys, and brain (FIG. 3I). The localization of DOPC nanoliposomes to tumors was further confirmed using Cy5.5-labeled siRNAs. This ability of DOPC nanoliposomes to preferentially deliver siRNAs to tumors while avoiding significant uptake in other organs is similar to that observed with several other systems, including pRNA nanoparticles. The pharmacokinetic analysis of MePS2-1-siEphA2-DOPC showed an Area Under the Curve (AUC)0-72 of 477 pg*h mL-1, Clearance (CL) of 5.23 L h−1, and Volume of distribution (Vd) of 26.3 L. Distribution half-life of MePS2-1-siEphA2-DOPC was 3.7 min and the elimination half-life was 9.3 h.

EXAMPLE 5

Targeting GRAMD1B for Ovarian Cancer Treatment

Having demonstrated that MePS2-1 siRNA has superior gene silencing activity compared to its UM counterpart for an established target, its silencing, and in turn therapeutic capability for a novel ovarian cancer target gene were next assessed. Since acquired chemoresistance is a major contributor to patient mortality from ovarian cancer (OvCa), targets playing substantial roles in this process are important targets. SiRNAs against approximately 22,000 individual genes were evaluated for their lethality and ability to induce taxane sensitivity in taxane-resistant epithelial ovarian cancer cells (SKOV3-TR) (data not shown). High correlation between cell viability score was observed across triplicate plates (median coefficient of variation=8.6%), indicating high data precision in the screen.

A total of 178 genes were identified to have reduced cell viability upon siRNA treatment and showed further cell death when combined with paclitaxel (data not shown). Importantly, the dose of paclitaxel used in the screen was IC30 of that achieved in parental taxane-sensitive SKOV3ip1 cells to permit identification of genes that, when silenced, can dramatically sensitize cells to taxane treatment. Out of 178 hits, eight genes were identified to be up-regulated in ovarian cancer epithelial cells compared to normal ovarian surface epithelial cells. Within this group, three genes associated with the highest lethality upon knockdown when combined with paclitaxel were focused on: GRAMD1B, RBBP6, and SLC23A1. Taxane-resistant ovarian cancer cell lines (HeyA8-MDR, SKOV3-TR) showed elevated levels of GRAMD1B mRNA and protein relative to their sensitive counterparts (HeyA8, SKOV3ip1). The expression of GRAMD1B remained unchanged for platinum resistant A2780-CP20 cells when compared to the parental line (A2780), indicating the lack of involvement of this gene in platinum resistance. GRAMD1B was also confirmed to be highly elevated in HeyA8 and SKOV3ip1 compared to the non-transformed HIO-180 ovarian epithelial cells. RBBP6 and SLC23A1 mRNA expression levels, though elevated in some ovarian cancer lines, were not found to be increased in resistant cell lines examined.

Figure 4A:
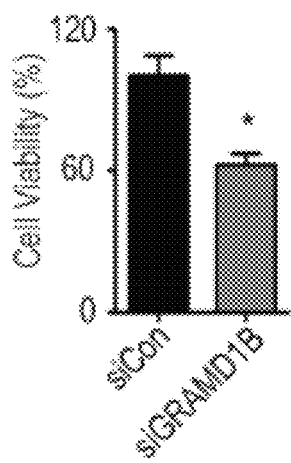
FIGS. 4A-C illustrate the effects of siGRAMD1B on silencing of GRAMD1B in the taxane-resistant cell line with the highest target expression, HeyA8-MDR.
Figure 4B:
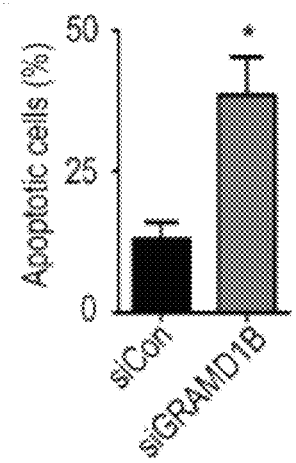
Figure 4C:
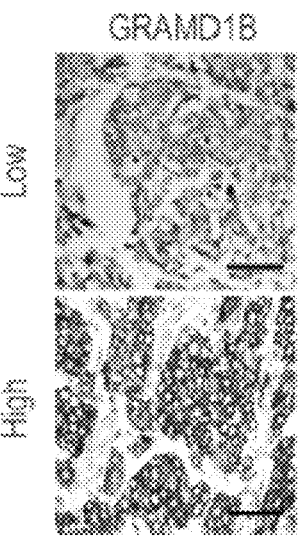
Figure 4D:
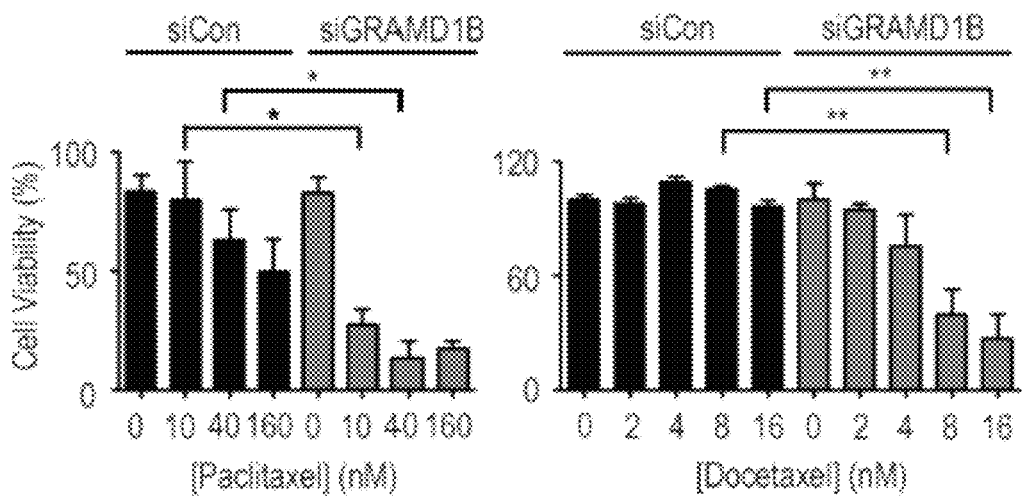
FIG. 4D shows the effects of siGRAMD1B on silencing of GRAMD1B in the taxane-resistant cell line with taxane sensitization using paclitaxel and docetaxel.

The effect of silencing GRAMD1B in the taxane-resistant cell line with the highest target expression was next examined, HeyA8-MDR (FIG. 4A, B, C). GRAMD1B silencing via introducing siGRAMD1B into cells using Lipofectamine 2000 exhibited both lethality as monotherapy (40% decrease in cell viability and 3-fold increase in apoptosis, FIG. 4 A, B) and also taxane sensitization at 10 nM paclitaxel (>75% vs. <5% cell death, siGRAMD1B plus paclitaxel vs. siCon plus paclitaxel) (FIG. 4D). Treatment with docetaxel produced a similar pattern. Significant taxane sensitization was also observed when another GRAMD1B-targeting siRNA was transfected into cells using another transfecting reagent, Lipofectamine RNAiMax. These results indicate the potential of GRAMD1B silencing in overcoming taxane resistance in ovarian cancer.

EXAMPLE 6

Therapeutic Effect of MePS2-1 siGRAMD1B In Vitro and In Vivo

Figure 5A:
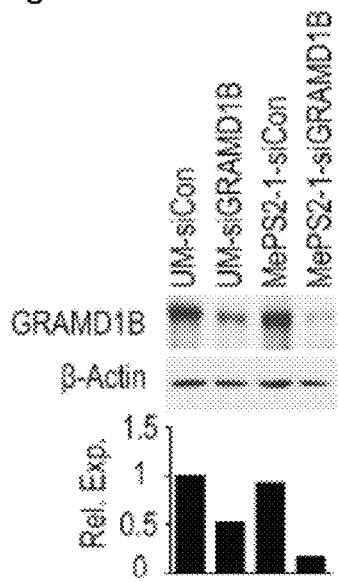
FIGS. 5A-C represent the ability of MePS2-1 modification to significantly enhance the silencing efficiency of UM siGRAMD1B.
Figure 5B:
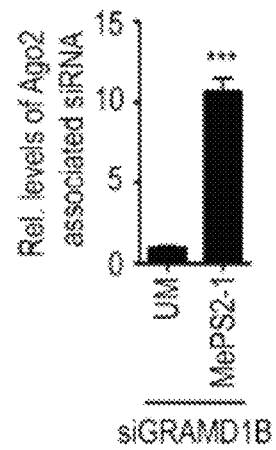

Having established the importance of targeting GRAMD1B in ovarian cancer treatment, the ability of MePS2-1 modification to significantly enhance the silencing efficiency of UM siGRAMD1B was examined. It was found that MePS2-1 siGRAMD1B efficiently silenced GRAMD1B both at the mRNA (70%, data not shown) and protein (85%) level in HeyA8-MDR cell line in the presence of serum (40 nM, FIG. 5A). This level of GRAMD1B knockdown was significantly better than that achieved by UM siGRAMD1B (85% vs. 50%). Consistent with findings using siEphA2 and siPTMS, MePS2-1 modification also significantly enhances the serum and intracellular stabilities of siGRAMD1B (FIG. 5D, E) and increases its binding to Ago2 protein when compared to UM siGRAMD1B (FIG. 5B). Let-7a was used as a normalizing control for the Ago2 binding study as its expression is not altered by GRAMD1B silencing.

Figure 5C:
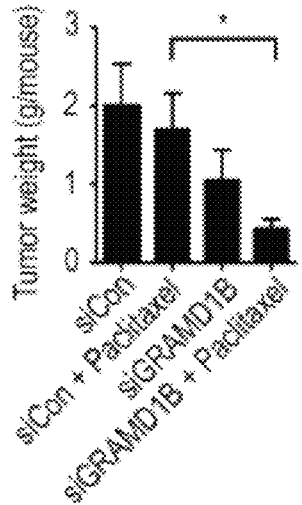
Figure 5D:
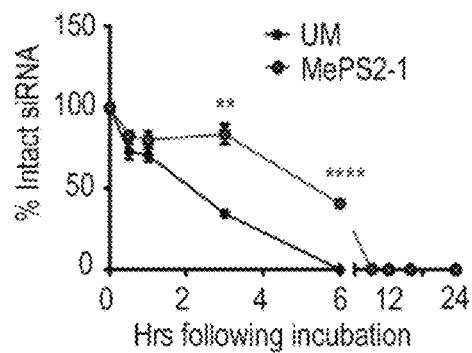
FIGS. 5D and E represent the stability of MePS2-1 modified siGRAMD1B in serum (D) and the intracellular stability of MePS2-1 siGRAMD1B (E).
Figure 5E:
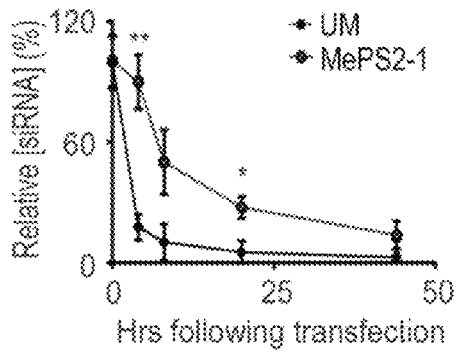

Moving into an orthotopic mouse model, HeyA8-MDR cells were injected into the peritoneal cavity and, after one week, mice were divided into 4 treatment groups: (a) MePS2-1-siCon-DOPC, (b) MePS2-1-siGRAMD1B-DOPC, (c) MePS2-1-siCon-DOPC plus paclitaxel, or (d) MePS2-1-siGRAMD1B-DOPC plus paclitaxel. Dosing was twice weekly for siRNA and weekly for paclitaxel (at a sub-therapeutic 100 μg dose), followed by tumor excision and quantification after five weeks of treatment. No significant reduction in tumor burden was observed for sub-therapeutic paclitaxel with MePS2-1-siCon-DOPC treatment group, as expected (FIG. 5C). However, MePS2-1-siGRAMD1B-DOPC alone resulted in 50% reduction in tumor burden, consistent with in vitro findings (FIG. 4A). Combining it with paclitaxel induced a 55% further reduction in total tumor weight compared to MePS2-1-siGRAMD1B-DOPC monotherapy, indicating the potential for taxane sensitization after GRAMD1B silencing. The reduction of GRAMD1B levels in tumors by MePS2-1-siGRAMD1B-DOPC was significant, with the protein level being down-regulated by 80% in tumors from mice treated with MePS2-1-siGRAMD1B-DOPC. This down-regulation of GRAMD1B in tumors was also significantly associated with the induction of cleaved caspase 3. This is consistent with the increased level of apoptotic cells observed following GRAMD1B silencing in vitro (FIG. 4B). Replicating the experiment with a different GRAMD1B-targeted siRNA sequence in SKOV3-TR, another taxane-resistant ovarian cancer model, produced a similar therapeutic effect. In this model, mice treated with both MePS2-1-siGRAMD1B-DOPC and paclitaxel had an 80% further decrease in tumor burden compared with mice treated with MePS2-1-siGRAMD1B-DOPC alone, which again indicated the role of GRAMD1B in taxane resistance. Importantly, in both of the models tested, there was no alteration in mouse body weights in any of the treatment groups.

EXAMPLE 7

Methods

Cell Lines:

The ovarian cancer cell lines, SKOV3ip1 and HeyA8, were obtained from ATCC and were maintained in RPMI 1640 supplemented with 15% fetal bovine serum and 0.1% gentamicin sulfate (Gemini Bioproducts; Calabasas, Calif.). SKOV3-TR and HeyA8-MDR were kind gifts from Dr. Isaiah Fidler, Department of Cancer Biology, University of Texas M. D. Anderson Cancer Center and Dr. Michael Seiden, Department of Medicine, Massachusetts General Hospital, respectively.

SiRNA Synthesis:

SiRNAs were synthesized at AM Biotechnologies. Modified and unmodified 21-nt RNAs (sense and antisense strands) were synthesized on the 1 μmole scale on an Expedite 8909 DNA/RNA Synthesizer using commercially available 5'-DMT-2'-O-TBDMS nucleoside ($A^{Bz}$, $C^{Ac}$, $G^{Ac}$, and U) phosphoramidite monomers and 5'-DMT-2'-O-Methyl nucleoside ($A^{Bz}$, $C^{AC}$, $G^{Ac}$, and U) phosphoramidite monomers as well as in house produced 5'-DMT-2'-O-Methyl nucleoside ($A^{Bz}$, $C^{Ac}$, $G^{Ac}$, and U) thiophosphoramidite monomers. See Yang, X. et al. "Gene silencing activity of siRNA molecules containing phosphorodithioate substitutions" ACS Chem. Biol. 7, 1214-1220 (2012); Wiesler, W. T. & Caruthers, M. H. "Synthesis of phosphorodithioate DNA via sulfur-linked, base-labile protecting groups" J. Org. Chem. 61, 4272-4281 (1996); Jackson, A. et al. "Position-specific chemical modification of siRNAs reduces 'offtarget' transcript silencing" RNA 12, 1197-1205 (2006).

Preparation of the Thiophosphoramidites:

5'-O-(4,4'-Dimethoxytrityl)-2'-O-(tert-butyldimethylsilyl) ribonucleosides were phosphitylated by means of tris-(pyrrolidino)phosphine (130 μL, 1.0 mmol) in the presence of 1H-tetrazole (0.35 mmol) in anhydrous dichloromethane (15 mL) containing a spatula of 3 Å molecular sieves for 15 min at RT. Trimethylsilylimidazole (15 μL, 0.1 mmol) was then added to the reaction mixture, and the reaction was stirred for 5 min. The resulting bis(pyrrolidino)phosphite intermediates were converted into the desired thiophosphoramidites (FIG. 1C, a-d) by treatment in situ with monobenzoylethanedithiol (220 μL, 1.3 mmol) and additional 1H-tetrazole (2.7 mmol). After an aqueous workup to remove 1H tetrazole and tetrazolide salts, the fully protected RNA thiophosphoramidites (FIG. 1C, 1a-d) were isolated by precipitation from hexane in 75-85% yield at more than 90% purity as assessed by $^{31}$P NMR. 1a ($B^Z$=Ade$^{Bz}$): yield, 85%, $^{31}$P NMR, δ=166.7, 174.2 ppm. 1b ($B^Z$=Cyt$^{4c}$): yield, 75%, $^{31}$P NMR, δ=168.4, 175.2. ppm. 1c ($B^Z$=Gua$^{4c}$): yield, 87%, $^{31}$P NMR, δ=163.8, 175.3 ppm. 1d ($B^Z$=Ura): 77%, $^{31}$P NMR, δ=170.01, 177.1 ppm.

Synthesis of RNA Containing PS2 Substitutions.

All PS2-modified RNAs were synthesized on 1000 Å controlled pore glass T support (resulting in a thymidine deoxyribonucleoside at the 3' end). The standard 2'-O-TBDMS RNA phosphoramidites were used for incorporation of A, C, G, and U residues. Each standard nucleotide was coupled using approximately 120 μL of a 0.1 M solution of the appropriate phosphoramidite in anhydrous acetonitrile. Each PS2 substitution was coupled using approximately 250 μL of a 0.15 M solution of the appropriate thiophosphoramidite in anhydrous acetonitrile, except that G thiophosphoramidite (1c) was prepared in anhydrous acetonitrile containing 10% anhydrous dichloromethane. All coupling times were 10 min. A 0.05 M solution of EDITH reagent in anhydrous acetonitrile was used as a sulfurizing agent to oxidize the internucleosidic thiophosphite to the phosporodithiotriester. See Ma, M. Y., et al. "Evaluation of 3-ethoxy-1,2,4-dithiazoline-5-one (EDITH) as a new sulfurizing reagent in combination with labile exocyclic amino protecting groups for solid phase oligonucleotide synthesis" Nucleic Acids Res, 25 (1997) 3590-3593.5.

A solution of 0.02 M $I_2$ in THF/pyridine/water was used to oxidize internucleosidic phosphites to phosphorotriesters. The average stepwise coupling efficiencies of all thiophosphoramidites were about 97% as estimated by the dimethoxytrityl cation assay. After completion of the synthesis, the solid support was suspended in ammonium hydroxide/methylamine (AMA) solution (prepared by mixing 1 volume of ammonium hydroxide (28%) with 1 volume of 40% aqueous methylamine) and heated at 65° C. for 15 min to release the product from the support and to complete the removal of all protecting groups except the TBDMS group at the 2'-position. The solid support was filtered, and the filtrate was concentrated to dryness.

The obtained residue was resuspended in 115 μL of anhydrous DMF and then heated for 5 min at 65° C. to dissolve the crude product. Triethyl amine (TEA—60 μL) was added to each solution, and the solutions were mixed gently. TEA.3HF (75 μL) was added to each solution, and the tubes were then sealed tightly and incubated at 65° C. for 2.5 h. The reaction was quenched with 1.75 mL of DEPC-treated water. The samples were analyzed by UV-Vis spectroscopy, and the OD readings were recorded.

Purification and Characterization of RNAs and PS2-RNAs:

Purification was performed on an Amersham Biosciences P920 FPLC instrument fitted with a Mono Q 10/100 GL column. The buffers were prepared with DEPC-treated water, and their compositions were as follows: Buffer A: 25 mM Tris-HCl, 1 mM EDTA, pH 8.0; Buffer B: 25 mM Tris-HCl, 1 mM EDTA, 1 M NaCl, pH 8.0. The FPLC gradient profile was as follows: 0-100% B over 50 min, 100% B for 5 min, 100-0% B over 5 min. Purified fractions were pooled and desalted via RP-HPLC on an Amersham Biosciences P900 fitted with a PRP-1 Column (Hamilton Co., Reno, Nev.). The buffers used were as follows: Buffer A: 0.1 M NH4OAc in DEPC-treated water, pH 7.0; Buffer B: HPLC grade acetonitrile. The gradient run was as follows: 0-35% B over 25 min, 35-0% B over 1 min. After desalting, the samples were frozen at −80° C. for 1 h, lyophilized, and dissolved in DEPC-treated water. All the RNA, PS-RNA and PS2-RNA oligonucleotides were characterized by denaturing polyacrylamide gel electrophoresis. Representative PS2-RNAs were further characterized by ESI-MS and 31P-NMR.

Preparation of SiRNA Duplexes.

Assembly of siRNA duplexes was performed in phosphate buffered saline (PBS) by heating the equivalent mixture of RNA oligonucleotides coding the sense and antisense strands of siRNA at 95° C. for 2 min followed by slow cooling to room temperature (over 2 h). The assembly of the resulting duplexes was confirmed by a 4% agarose gel electrophoresis. For in vivo experiments, ammonium counter cation was replaced by sodium cation.

In vitro siRNA transfection and luciferase assays: Cells were transfected with 10-100 nmol L$^{-1}$ of specified siRNAs using Lipofectamine 2000 or Lipofectamine RNAiMax reagent (Invitrogen) at 3 μL reagent: 1 μg siRNA ratio. Cells were treated with siRNAs for 4 h in serum-free or 10% FBS-containing media before incubation in fresh complete media for the specified timeframe. GoClone pLightSwitch luciferase reporter constructs containing AS and S siRNA target sequences were obtained from SwitchGear genomics (Menlo Park, Calif.).

Antisense (AS) construct contains the following sequence:

SEQ. ID. NO. 57
5'-CAAAGGGTGGGACCTGATGCAGAACATCATGAATGACATGCCGATCT ACATGTACTCCGTGTGCAACGTGATGTCTGGCGAC-3'..

Sense (S) construct contains the following sequence:

SEQ. ID. NO. 58
5'-ACCTGATGCAGAACATCATGAACATGTAGATCGGCATGTCATACTCC GTGTGCAACGTGATGTCT-3'..

SKOV3ip1 cells were transfected with FuGENE HD reagent in a 96-well plate with specified siRNAs (100 nM) along with S or AS reporter construct, and Cypridina TK control construct (pTK-Cluc). After 24 h of transfection, luciferase activity was obtained using LightSwitch Dual Luciferase assay kits. Luciferase activity was normalized with the Cypridina TK control construct. All assays were performed in triplicate.

Quantitative Reverse Transcription-Polymerase Chain Reaction:

RNA was isolated from cells, Ago2 pull down products, blood samples, and tissues using Trizol (Invitrogen) according to the manufacturer's protocol. Using 1 µg of RNA, cDNA was synthesized by using a Verso cDNA kit (Thermo Scientific) as per the manufacturer's instructions. Analysis of mRNA levels was performed on a 7500 Fast Real-Time PCR System (Applied Biosystems) with SYBR Green-based qRT-PCR. PCR was performed with reverse-transcribed RNA and 100 ng µL-1 of forward and reverse primers in a total volume of 20 µL. Each cycle consisted of 15 s of denaturation at 95° C. and 1 min of annealing and extension at 60° C. (40 cycles). Stem loop PCRs for siRNA detection were performed using TaqMan miRNA assays followed by SYBR Greenbased qRT-PCR41. For miRNA quantification, total RNA was isolated using Trizol (Invitrogen) extraction. TaqMan miRNA assays (Applied Biosystems) were used for reverse transcription and qRT-PCR was performed according to the manufacturer's instructions. For microRNA detection, Ambion assay probe sets were used according to the manufacturer's protocol. The relative amount of mRNA/siRNA in each sample was normalized to β-actin mRNA, RNU44, RNU6B, or respective microRNAs.

Melting Profiles of siRNAs:

Certain of the absorption measurements were performed in a 1-cm path length cell with a Cintra 4040 spectrophotometer equipped with a Peltier Thermocell (GBC, Dandenong, Australia). Complementary RNA strands were mixed in 10 mM Tris-HCl buffer (pH 7.4) with 100 mM NaCl, and 0.1 mM Ethylenediaminetetraacetic acid (EDTA) at a final concentration of 2 µM (0.8 OD of both mixed strands). Annealing was performed at a temperature gradient of 1.5° C./min, from 85 to 15° C. Melting profiles were measured using a temperature gradient of 1° C./min, from 15 to 85° C., with the detector set at 260 nm. Each Tm reported was an average of values from three to six independent experiments.

Circular Dichroism Measurements:

Circular Dichroism (CD) spectra were recorded on a CD6 dichrograph (Jabin-Yvon) using cells with 0.5 cm path length, 2 nm bandwidth, and 1-2 s integration time. Each spectrum was smoothed with a 25-point algorithm. The spectra from 200-340 nm were recorded at 25° C. in the same buffer as in the melting experiments (n=3). The concentration of the two complementary RNA oligonucleotides was ca. 2 µM.

Western Blot:

Protein lysates were prepared from cultured cells or tumors using modified RIPA buffer (50 mM Tris-HCl (pH 7.4), 150 mM NaCl, 1% Triton, 0.5% deoxycholate) plus 25 µg mL$^{-1}$ leupeptin, 10 µg mL$^{-1}$ aprotinin, 2 mM EDTA, and 1 mM sodium orthovanadate. Membranes were probed with primary antibodies against EphA2 (1:1000, Millipore, 05-480), β-actin (1:5000, Sigma, A5316), vinculin (1:2500, Sigma, V9131), GAPDH (1:5000, Sigma, G8795), Ago2 (1:100, Wako Chemicals, 015-22031), and GRAMD1B (1:500, Sigma, HPA008557) in 5% skim milk in TBS-T. Quantification was performed using ImageJ.

Intracellular Ago2 Binding Study:

Cells were lysed at 7 h post-transfection using ice-cold lysis buffer (50 mM Tris-HCl at pH 7.5, 200 mM NaCl, 0.5% Triton, 2 mM EDTA, 1 mg mL$^{-1}$ heparin, and protease inhibitor cocktail). Ago2 antibody (Wako Chemicals, 015-22031, 20 µL) was absorbed onto magnetic protein G Dynabeads (Invitrogen, 40 µL) by incubation at 4° C. for 2 h on a rotator. The beads were then washed twice with lysis buffer to remove unbound antibodies. Following washing, beads were incubated with protein lysate (360 µg) overnight at 4° C. on a rotator. Following removal of unbound proteins, bound material was eluted from beads using 50 µL of 0.1 M glycine (pH 2.3) for 15 min at RT. Eluted fractions were neutralized immediately with an equal volume of 1 M Tris-HCl (pH 8) and then treated with 20 U of proteinase K for 10 min at 65° C. The amount of Ago2-bound siRNA was then quantified using stem loop PCR technique. For the biotin-siRNA pull down experiment, strepavidin beads were blocked and incubated with cell lysates at 4° C. for 2 h. The amount of siRNA-associated Ago2 was quantified via Western blotting.

Serum Stability Assay:

SiRNAs (1.33 µg) were incubated in 10 µL, of 10% FBS in PBS at 37° C. for up to 24 h. All samples were separated in 20% polyacrylamide gels. The percentage of intact siRNA present was quantified using ImageJ.

Immunogenicity of siRNAs:

Bone marrow progenitor cells were isolated from C57BL/6 mice and were differentiated into dendritic cells in vitro for 7 days using FLT3 ligand (100 ng mL$^{-1}$; Pepro-Tech). Cells were treated with 75 nM of siRNAs for 6 h in serum-free media using RNAiMax™. A high interferon-inducing siRNA sequence (BP1Mod2) and CpG2216 (1 µg mL-1, Sigma) were used as positive controls. The level of IFN-α and TNF-α in the culturing media was assessed using murine IFN-α and TNF-α ELISA kits at 2, 6, and 24 h following transfection (R&D Systems). For TLR7 experiments, peripheral blood mononuclear cells (PBMCs) were obtained from wild-type and TLR7-KO C57BL/6 mice and were treated with 75 nM of siRNAs for 6 h. IFN-α and TNF-α levels in the culturing media was measured 24 h post-transfection. For in vivo studies, serum was collected from mice at 2, 6, and 24 h post siRNA treatment and IFN-α and TNF-α levels were measured as described above.

Liposomal Nanoparticle Preparation:

SiRNAs for in vivo delivery were incorporated into DOPC liposomes essentially according to the method of Landen, C. J. et al. "Therapeutic EphA2 gene targeting in vivo using neutral liposomal small interfering RNA delivery" *Cancer Res.* 65, 6910-6918 (2005). DOPC and siRNA were mixed in the presence of excess tertiary butanol at a ratio of 1:10 (w/w) siRNA/DOPC. Tween 20 was added to the mixture in a ratio of 1:19 Tween 20:siRNA/DOPC. The mixture was vortexed, frozen in an acetone/dry ice bath, and lyophilized. Before in vivo administration, this preparation was hydrated with PBS.

Orthotopic In Vivo Models of Ovarian Cancer:

Female athymic nude mice (8-12 weeks old) were obtained from the National Cancer Institute, Frederick Cancer Research and Development Center (Frederick, Md.). All mouse studies were approved and supervised by the M.D. Anderson Cancer Center Institutional Animal Care and Use Committee. For therapeutic experiments, ten mice were assigned per treatment group. This sample size gave 80% power to detect a 50% reduction in tumor weight with 95% confidence. To establish intraperitoneal tumors, cells were injected into the peritoneal cavity (i.p.) at a concentration of $5 \times 10^6$ cells $mL^{-1}$ (200 μL per injection). All mice were treated with siRNAs (2.5 or 5 μg for EphA2 and GRAMD1B experiments, respectively) twice weekly beginning at one week following tumor cell injection. Paclitaxel (100 μg) was injected i.p. once weekly. Mice (n=10 per group) were monitored for adverse effects and tumors were harvested after 5 weeks of therapy or when any of the mice began to appear moribund. Mouse weight, tumor weight, and the number/location of tumor nodules were recorded. Tumor tissues were fixed in formalin for paraffin embedding or were snap frozen for lysate preparation. For gene silencing (1.25 and 2.5 μg), immune toxicity (5 μg), pharmacokinetic (2.5 μg), and biodistribution studies (2.5 μg), a single dose of siRNA was administered i.p. once tumors became palpable. Blood and/or tissues samples were collected at specified time points for RNA/protein extraction or ELISA assay. For the fluorescence-based biodistribution study, Cy5.5-labeled siRNAs were administered i.p. and 48 h later, fluorescence imaging of excised tumor and organs was performed using the Xenogen IVIS 200 system. Cy5.5 fluorophore excitation (678 nm) and emission (703 nm) filters were used. Using Living image 2.5 software, regions of interest were drawn for each organ and the total radiant efficiency $ps^{-1}$ $\mu W^{-1}$ $cm^2$ was measured.

Pharmacokinetic Analysis:

Blood concentrations of siRNA at the indicated times, C(t), were expressed as pg siRNA per mL of blood. Pharmacokinetic parameters were determined by fitting the C(t) with a two-compartment model using the MULTI program. The area under the blood concentration-time curve (AUC) was calculated by integration of C(t) up to 72 h following administration. Vd was calculated by dividing the injected dose by C(0). CLtotal was calculated by dividing injected dose by AUC.

Microarray and Pathway Enrichment Analysis:

HeyA8-MDR cells were treated with siGRAMD1B and total RNA was extracted 48 h following transfection using mirVana RNA isolation labeling kit (Ambion). Five hundred nanograms of total RNA were used for labeling and hybridization on a Human HT-12 v4 Beadchip (Illumina) according to the manufacturer's protocols. After the bead chips were scanned with an Illumina BeadArray Reader (Illumina), the microarray data were normalized using the quantile normalization method in the Linear Models for Microarray Data (LIMMA) package in the R language environment. The expression level of each gene was transformed into a log 2 base before further analysis. GEOID for the microarray data is GSE54459. The top ten pathways perturbed by siGRAMD1B treatment were identified using NetWalker software. Each interaction in the global network of biological relationships was scored based on combined assessment of the network connectivity and the input data. Biological pathways were ranked based on geometric P-values.

SiRNA Lethality Screen:

SKOV3-TR cells used for the screen were maintained in antibiotic-free RPMI1640 supplemented with 10% fetal bovine serum48 and were authenticated prior to their utilization in the screen. For the screen, SKOV3-TR (2,000 cells per well) were transfected using siRNAs in individual wells of black 384-well plates for 48 h. Transfection was performed using a pool of 4 individual siRNAs targeting individual genes (siGenome Smart pool, G-004605, Dharmacon) using Dharmafect 1 (Dharmacon). SiTOX was used as a control for transfection efficiency. Non-targeting siRNA number 4 (siOTP4, Dharmacon) was used as a transfection control in all experiments. In summary, 0.2 μL of 20 μM siRNA was mixed with 0.2 μL of Dharmafect 1 and 20 μL of Optimem medium (Invitrogen) for 20 min in a well of 384-well plate and overlaid with 80 μL of cell suspension (2,000 cells) in antibiotic-free RPMI1640 supplemented with 10% fetal bovine serum. This gave a final siRNA concentration of 40 nM per well. For each plate, 4 types of control were included: siOTP4 as a negative control (16 wells), siTOX as a control for transfection efficiency (8 wells), cells only (24 wells), and blank wells (16 wells). Following siRNA treatment, cells were treated with paclitaxel (3.5 nM). All experiments were performed at 37° C. in the presence of 5% CO2. Finally, cell viability was determined using 3-(4,5-dimethylthiazol-2-yl)-2,5-diphenyltetrazolium bromide (MTT, USB Corporation) as per manufacturer's instruction three days after treatment and signal was detected using a PHERAstar FS plate reader (BMG Labtech). Following data collection, the values in each plate were centered on 100 using median scaling and cell viabilities were expressed as percentages of siOTP4 treated samples. Student's t-test was used to examine chemosensitization following conversion of raw values to log 2 scale.

Cell Viability Assays:

HeyA8-MDR cells were transfected with siRNAs (100 nM) on day 1 and 3 before paclitaxel or docetaxel treatment. Cell viability was assessed three days following taxane treatment using MTT assay as per manufacturer's protocol.

Statistical Analysis:

Kaplan-Meier plots were constructed and a log-rank test was used to determine differences among survival curves according to tumoral GRAMD1B expression level. Contingency tables and Fisher's exact test or Chi-square test were used to evaluate the relationship between death and categorical variables. Multivariate analyses were performed with the use of a Cox proportional-hazards model to examine the effects of tumoral GRAMD1B expression on death from disease while adjusting for other covariates. Chi-square test was performed to assess the effect of tumoral GRAMD1B expression on drug response. For siRNA lethality screen, student t-test was used to examine chemosensitization following conversion of raw values to log 2 scale. For other assays, student's t-test was performed to examine the difference between control and treatment groups.

Apoptosis Assay:

Apoptosis was studied using the Annexin V apoptosis detection kit (BD Biosciences) according to the manufacturer's protocol. Apoptotic cells were analyzed using a FACSCalibur flow cytometer (BD Biosciences). CellQuest Pro software (BD Biosciences) was used to determine the number of apoptotic cells.

Modeling of siRNA:PAZ Domain Interactions:

Coordinates of the complex between a 9 mer siRNA and the PAZ domain from human Argonaute eIF2c1 were retrieved from the Protein Data Bank (http://www.rcsb.org; PDB ID code 1si2). The program UCSF Chimera was used to convert the sequence of the last four nucleotides in the siRNA from the 1si2 crystal structure to match the sequence and chemistry of MePS2-1 ( . . . ACUdCdU-3' and . . . AUMeS2GMeS2dTdT-3', respectively).

Changes to reflect the chemistries of the Me-1 and PS2-1 siRNAs were accomplished in a similar manner. Side chain torsion angles of C270 and M273 were adapted in USCF Chimera, and the program was used for measuring distances and producing figures.

The complex models generated were not subjected to energy minimization with either molecular mechanics or dynamic approaches. The important role of M273 in stabilizing the siRNA:PAZ interaction is reflected by the reported change in Kd upon mutation of residue 273 from methionine to alanine Ma, J., Ye, K. & Patel, D. "Structural basis for overhang-specific small interfering RNA recognition by the PAZ domain" Nature 429, 318-322 (2004). The side chain of M273 snakes along the terminal base pair of the siRNA duplex, and the mutation to alanine abolishes this stacking interaction and doubles the Kd. The effect of hydrophobic interactions between siRNAs and M273/C270 on Kd was also examined.

EXAMPLE 8

Further Analysis of Mechanisms of Benefits Seen with MePS2 Modification

Crystal structures of PS2- and MePS2-modified RNAs were undertaken and revealed subtle changes in geometry and hydration compared with natural RNA. The model of an MePS2-RNA:PAZ domain complex disclosed herein points to a hydrophobic effect as the source of the higher affinity of MePS2-RNA for Ago2.

Chemical modification of the antisense (guide) and/or sense (passenger) siRNA strand modulates RNA affinity, nuclease resistance, immune stimulation, uptake and biodistribution, and is widely expected to be required for efficacy in vivo. SiRNAs containing phosphorodithioate modifications (PS2-RNA) were recently shown to exhibit favorable properties for therapeutic applications.

Thus, the PS2 moiety, despite destabilizing the duplex slightly relative to the native phosphate (PO2), appears not to distort the A-form geometry, improves serum stability, and is tolerated in the central part of the antisense strand as well as in most of the positions tested in the sense strand.

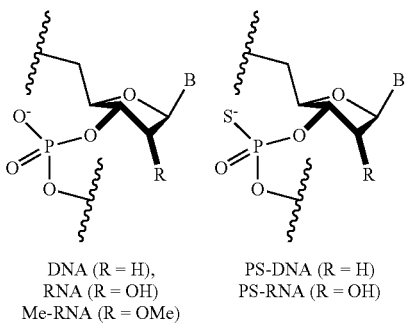

DNA (R = H),
RNA (R = OH)
Me-RNA (R = OMe)

PS-DNA (R = H)
PS-RNA (R = OH)

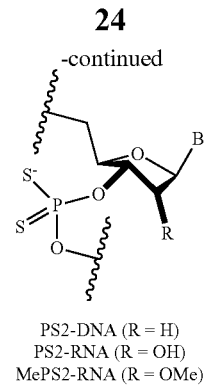

PS2-DNA (R = H)
PS2-RNA (R = OH)
MePS2-RNA (R = OMe)

Unlike the phosphorothioate moiety (PS, shown above), PS2 is achiral, thus precluding potential drawbacks that may arise from chiral P-substituted oligonucleotides, owing to variable biophysical and biochemical properties of individual (e.g. PS-) diastereoisomers. In addition, PS2-modified siRNAs display increased protection against degradation by nucleases compared with PS-modified oligonucleotides. Combining the PS2 with the 2'-O-methyl ribose modification (MePS2-RNA, above) afforded increased loading of modified siRNA duplexes into the RNA-induced silencing complex (RISC) as well as enhanced anti-tumor activity. Further efforts were undertaken to understand the basis of this benefit.

Synthesis of Native and Me-, PS-, PS2- and MePS2-Modified siRNAs:

The siRNA and modified RNAs were synthesized on an Expedite 8909 DNA/RNA Synthesizer using commercial 5'-DMT-2'-O-TBDMS nucleoside ($A^{Bz}$, $C^{Ac}$, $G^{Ac}$, and U) phosphoramidite monomers as well as 2'-OMe-thiophosphoramidites. The average stepwise coupling efficiency of all phosphoramidites including thiophosphoramidites was about 97% as estimated by the DMT-cation assay. After deprotection, all of the modified RNAs were isolated by FPLC according to Yang, X.; et al. ACS Chem. Biol. 2012, 7, 1214-1220 and Wu, S. Y.; Yang, X.; et al. Nat. Comm. 2014, 5, 3459. The PS2-RNAs were desalted using reverse-phase HPLC to yield the PS2-RNA final products. The representative structures of the MePS2-RNAs were confirmed by ESI-MS. Assembly of siRNA duplexes was performed in ammonium acetate buffer (pH 7.4) by heating the equivalent mixture of RNA oligonucleotides coding for the sense and antisense strands of siRNA at 90° C. for 2 min, followed by slow cooling to room temperature (over 2 h). Assembly of the resulting duplexes was confirmed by electrophoresis using a 4% agarose gel.

$T_m$ measurements were undertaken as previously described herein. The results for melting temperature studies of the following sequence are shown in Table 4 below.

TABLE 4

Melting temperatures $T_m$ of native and MePS2-siRNAs

| RNA | Sequence | SEQ. ID. NO. | $T_m$ [° C.] |
|---|---|---|---|
| siRNA-1$^{Bet}$ | 5' AUA CAG GCA GCA GUA ACU UU TT 3' | 59 | 73.7 ± |
|  | 3' TT UAU GUC CGU CGU CAU UGA AA 5' | 60 | 0.8 |
| MePS2-1$^{Bet}$ | 5' AUA CAG GCA GCA GUA ACU U$_{MePS2}$U$_{MePS2}$TT 3' | 61 | 74.0 ± |
|  | 3' TT UAU GUC CGU CGU CAU UGA A   A 5' |  | 0.2 |

TABLE 4-continued

Melting temperatures $T_m$ of native and MePS2-siRNAs

| RNA | Sequence | SEQ. ID. NO. | $T_m$ [° C.] |
|---|---|---|---|
| MePS2-3$^{Bet}$ | 5' AUA CA$_{MePS2}$GGCAG$_{MePS2}$CAGUA$_{MePS2}$ACU UU$_{MePS2}$TT 3'<br>3' TT UAU GU    CCGUC    GUCAU   UGA   AA 5' | 62 | 73.7 ± 0.5 |
| MePS2-4$^{Bet}$ | 5' AUA CAG GCA GCA GUA AC  U   UU TT 3'<br>3' TT UAU GUC CGU CGU CAU UG$_{MePS2}$A$_{MePS2}$AA 5 ' | 63 | 74.2 ± 0.8 |
| MePS2-9S$^{Bet}$<br>MePS2-9AS$^{Bet}$ | 5' AUA$_{MePS2}$CAG GCA GCA$_{MePS2}$GUA ACU UU TT 3'<br>3' TT UAU    GUC CGU CGU$_{MePS2}$CAU UGA AA 5' | 64<br>65 | 74.4 ± 0.5 |
| MePS2-3$^{Bet}$<br>MePS2-11$^{Bet}$ | 5' AUA CA$_{MePS2}$GGCA   G$_{MePS2}$CAGUA$_{MePS2}$ACU UU$_{MePS2}$TT 3'<br>3' TT UAU GU   CCGU$_{MePS2}$C$_{MePS2}$GUCAU UGA AA 5' | 62<br>66 | 73.2 ± 0.2 |

Ago2 Affinity Assays:

The antisense strand siRNA was biotinylated at its 3'-terminus, allowing immobilization of an annealed duplex on to a streptavidin (SA) coated sensor surface. This enabled kinetic analysis of siRNA duplex binding to Ago2 on a fortéBIO Octet Red96 instrument set at 30° C. Samples were agitated at 1000 rpm. The annealing method, binding buffer condition, siRNA loading concentration, siRNA loading time, Ago2 titer range, appropriate blocking reagent, blocking time, Ago2 stability over assay duration, and octet baseline correction methods were thoroughly investigated and optimized in the current study. Ago2 in HSCMT was prepared as a dilution series (0, 12.5, 25, 50, 100, and 200 nM) along with HSCMT buffer blanks (unloaded sensor controls). Association was monitored for 300 sec and dissociation was followed for 300 sec. If necessary, the dissociation was stretched to at least 900 sec to verify tight binding. The data were fit to a 1:1 binding model using fortéBIO Octet data analysis software. Kinetic constants were determined by integration of the experimental data using the differential rate equation $dR/dt = k_{on} \cdot C \cdot (R_{max} - R) - k_{off} \cdot R$ to obtain both the $k_a$ and $k_a$ values (R=observed response, $R_{max}$=maximum response upon saturation, C=analyte concentration, $k_{on}$=association rate constant, $k_{off}$=dissociation rate constant). The ratio between $k_{off}$ and $k_{on}$ corresponds to the reported dissociation constants ($k_{off}/k_{on} = K_D$). The goodness of the fit was judged by the reduced $\chi^2$ and $R^2$ values.

CD Measurements:

CD spectra were recorded on a CD6 dichrograph (Jobin-Yvon, Longjumeau, France) using cells with 0.5 cm path length, 2 nm bandwidth, and 1-2 sec integration time. Each spectrum was smoothed with a 25-point algorithm (included in the manufacturer's software, version 2.2.1) after averaging of at least three scans. The spectra from 200 nm to 340 nm were recorded at 25° C. in the same buffer used for the melting experiments. The concentration of the two complementary RNA oligonucleotides was ca. 2 µM.

Modeling of PAZ:siRNA Complexes:

Coordinates for the crystal structure of a self-complementary RNA with a 3'-dCT overhang bound to the human Ago2 PAZ domain were obtained from the Protein Data Bank (http://www.rcsb.org/pdb/home/home.do; PDB ID 1si2). Using the program UCSF Chimera, non-canonical Py:Py and Pu:Pu pairs were replaced by Watson-Crick pairs according to the EphA2 siRNA sequence (Table 5), and the 2'-deoxy-C in the 3'-overhang was replaced by T.

TABLE 5

Human Ago2 binding affinities of EphA2 siRNAs with various sense strand modifications adjacent to the 3'-overhang

| sRNA ID | Sequence: -B-=Biotin | SEQID. NO. | $K_D$ |
|---|---|---|---|
| AF163A | 5'-UGA CAU GCC GAU CUA CAU$_{MePS2}$ G$_{MePS2}$dTdT-3'<br>3'-B-dTdT ACU GUA CGG CUA GAU GUA    C-5' | 67<br>68 | 21.1 pM$^a$ |
| AF163B | 5'-UGA CAU GCC GAU CUA CAU GdTdT-3'<br>3'-B-dTdT ACU GUA CGG CUA GAU GUA C-5' | 69 | 0.6 µM |
| AF163C | 5'-UGA CAU GCC GAU CUA CAU$_{MePS}$ G$_{MePS}$dTdT-3'<br>3'-B-dTdT ACU GUA CGG CUA GAU GUA    C-5' | 70 | 41.1 nM |
| AF163D | 5'-UGA CAU GCC GAU CUA CAU$_{PS2}$ G$_{PS2}$dTdT-3'<br>3'-B-dTdT ACU GUA CGG CUA GAU GUA    C-5' | 71 | 12.4 pM$^a$ |
| AF163F | 5'-UGA CAU GCC GAU CUA CAU$_{PS}$ G$_{PS}$dTdT-3'<br>3'-B-dTdT ACU GUA CGG CUA GAU GUA    C-5' | 72 | 14.5 nM |

$^a$The PS2- and MePS2-siRNA affinities based on bio-layer interferometry are similar, although those from cellular Ago2 association or pull-down assays consistently show tighter binding by MePS2-modified RNAs.

In addition all water molecules were removed and hydrogen atoms were added. Following rebuilding of the RNA, the native complex was subjected to minimization by steepest descent and conjugate gradient using the Amber ff12SB force field in Chimera. In the complex with the MePS2- modified sense strand, two phosphates adjacent to the 3'-overhang were replaced by phosphorodithioate moieties (taken from the crystal structure of CPs2G-RNA). In addition, methyl groups were added to the 2'-oxygen atoms, such that the conformation of the CH3-O2'-C2'-C3' torsion angle is in the antiperiplanar range. The complex was subsequently subjected to refinement as described above for the native PAZ:siRNA complex.

Crystallization Experiments:

To gain insight into the conformational consequences of PS2 modification and potential changes as a result of combining it with the ribose 2'-O-methyl substitution, crystal structures were determined of the RNA duplexes (CGC$_{PS2}$GAAUUAGCG (SEQ. ID. NO.73))$_2$(C$_{PS2}$G-RNA), (CGCGA$_{MePS2}$AUUAGCG (SEQ. ID. NO.74))$_2$ (A$_{MePS2}$A-RNA), and (CGCGAAUUA$_{MePS2}$GCG (SEQ. ID. NO. 75))$_2$ (A$_{MePS2}$G-RNA) at resolutions of between 1.13 and 1.19 Å.[‡] The structures were phased by molecular replacement, using a previously determined structure of the native RNA as search model.

The above referenced modified RNA dodecamers were dissolved in deionized water and the stock concentrations adjusted to ca. 1.2 mM. Crystallization trials were performed with the hanging drop vapor diffusion technique, using the 24 conditions of the Nucleic Acid Miniscreen (Hampton Research Inc., Also Viejo, Calif.).[5] Droplets (1 µL) of modified RNA dodecamer were mixed with droplets of equal volume of the individual sparse matrix screen solutions and equilibrated against 0.6 mL of a 35% v/v solution of 2-methyl-2,4-pentanediol (MPD) at 18° C. The optimal crystallization conditions for the three oligonucleotides were as follows. CPS2G-RNA: condition 20; sodium cacodylate buffer, pH 7.0, 80 mM sodium chloride, 20 mM barium chloride, 12 mM spermine tetrahydrochloride, and 10% v/v MPD. A$_{MePS2}$A-RNA: condition 15; 40 mM sodium cacodylate pH 7.0, 12 mM spermine tetrahydrochloride, 80 mM potassium chloride, and 10% v/v MPD. A$_{MePS2}$G-RNA: condition 8; 40 mM sodium cacodylate, pH 6.0, 80 mM sodium chloride, 12 mM spermine tetrahydrochloride, and 10% v/v MPD.

X-Ray Data Collection, Structure Determination and Refinement:

Crystals were mounted in nylon loops, flash-frozen in liquid nitrogen without further cryo-protection and stored in liquid nitrogen prior to data collection. Diffraction data were collected on the 21-ID-F or 21-ID-G beam lines of the Life Sciences Collaborative Access Team (LS-CAT) at the Advanced Photon Source (APS), located at Argonne National Laboratory (Argonne, Ill.), using MARCCD 225/300 detectors. The wavelength was 0.98 Å and crystals were kept at 100K during data collection. Diffraction data were integrated, scaled and merged using HKL2000.6. Selected data collection and refinement statistics are listed in FIG. 8. The structure was determined by the molecular replacement method with the program MOLREP7 in the CCP4 suite of crystallographic software, using the native RNA dodecamer as the search model (PDB ID 2Q1R9; http://www.rcsb.org). Following initial positional and isotropic temperature factor refinements with the program REFMAC, the R-work dropped to the mid 20s and R-free to the upper 20s. After further refinement in REFMAC, refinements were continued with SHELX. The phosphorodithioate and 2'-O-methyl moieties (the asymmetric unit contains a single strand) were built into Fourier (2Fo-Fc) sum and (Fo-Fc) difference electron density maps that were visualized with COOT12 and the refinement was continued after adaptation of the dictionary files. Further refinements were carried out and after each refinement the nucleotides and water molecules were checked for possible alternate conformations/positions and corrections were made where necessary. A final refinement was carried out with all nucleic acid atoms and water molecules being treated with anisotropic B-factors and these refinement parameters are summarized in FIG. 8. All figures were generated with the program UCSF Chimera.

Interestingly, it was determined that the increased loading of modified siRNA duplexes into the RNA-induced silencing complex (RISC) obtained by combining the PS2 with the 2'-O-methyl ribose modification (MePS2-RNA, above) can be attributed to MePS2 modification at two residues adjacent to the 3'-TT overhang in the sense siRNA strand. This conclusion is supported by higher association (based on in vitro pull-down assays), and tighter intracellular binding between MePS2-siRNA and Ago2 protein, relative to the corresponding P02, PS2-, or methoxy-modified RNAs (RNA, PS2-RNA, or Me-RNA). MePS2-siRNA showed significantly enhanced silencing of EphA2 involved in taxane resistance compared to all other RNA chemistries in both the SKOV3ip1 and HeyA8 epithelial ovarian cancer cell lines that highly express target protein. Other proteins with a key role in chemo-resistance besides EphA2, such as GRAMD1B, were subsequently targeted by systemic administration of MePS2-siRNA, leading to a re-sensitization of chemo-resistant ovarian tumors to taxane therapy.

The data showed that the structures of the PS2-modified RNA duplexes are isomorphous with that of the native RNA. Thus, the duplex is located on a crystallographic dyad and a single dodecamer strand constitutes the asymmetric unit. Superimposition of the CPS2G and native RNA duplexes demonstrated their virtually identical conformations (data not shown). In particular PS2 modification does not trigger any changes in the ribose conformation and the backbone torsion angles. The most obvious deviation concerned the P—S bond lengths in the phosphorodithioate moiety (ca. 1.94 Å) compared to the P—O bonds in the native phosphate (ca. 1.60 Å)

Figure 7A:
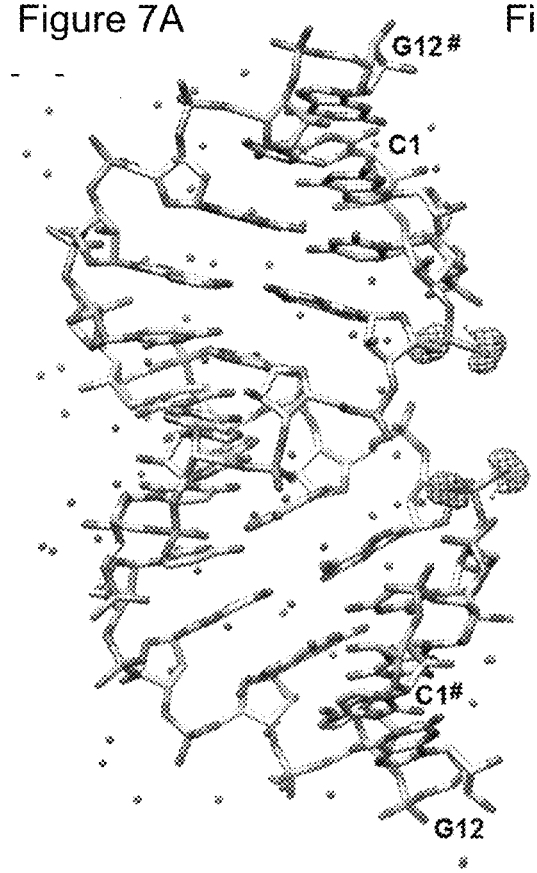
FIGS. 7A-C shows crystal structures of the described CPs2G-RNA duplex.
Figure 7B:
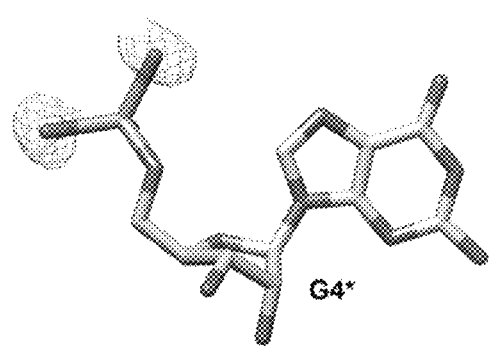
Figure 7C:
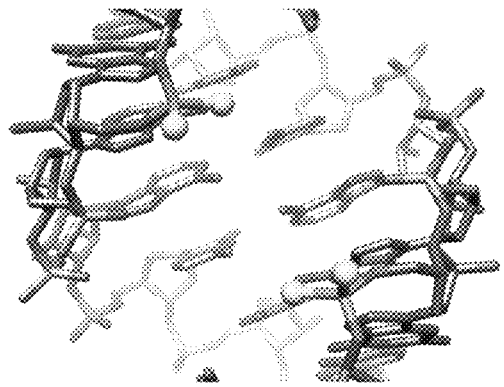

Crystal structures of the C$_{PS2}$G-RNA duplex are depicted in FIG. 7 A-C. FIG. 7A shows a view across the major and minor grooves. Fourier Fo-Fc difference electron density (2.5σ level) around O1P and O2P of G4 and G16 (indicating the presence of sulfur) is depicted as a meshwork, terminal residues are labeled, and water molecules are small spheres. FIG. 7B shows a close-up view of residue G4 with difference density around O1P and O2P before incorporation of sulfur. FIG. 7C shows a view into the central major groove with sulfur atoms shown as balls.

It was further shown that, in the A$_{MePS2}$A- and A$_{MePS2}$G-RNA duplexes, 2'-O-methyl groups are directed into the minor groove, a result of the familiar ap orientation around the C2'-O2' bond. Therefore, neither the PS2 modification alone nor the combination of the PS2 and 2'-O-methyl modifications appear to have a notable effect on the conformation of A-form RNA judging from the crystallographic results.

However, the 2'-O-methyl modification can offset the slight thermodynamic destabilization caused by the PS2 moiety compared with the native RNA duplex. We determined the melting temperatures ($T_m$) of siRNAs containing two to six MePS2 modifications and found that they exhibit thermal stabilities that are comparable to that of the unmodified RNA (PO2) (Table 4 above).

To assess potential conformational consequences of the MePS2 modification in solution, we measured the circular dichroism (CD) spectra of the siRNA duplexes listed in Table 4. All spectra were closely similar to the spectrum of the native duplex and are consistent with the typical A-type structure (a maximum of the positive Cotton effect at 268 nm and a crossover point at 240 nm.

The lack of an obvious change in both the conformation and stability of MePS2-RNA relative to native RNA points to another cause of the favorable therapeutic properties of this modification. To better understand the increased Ago2 affinity of siRNA containing MePS2-modified sense strands, we built models of PAZ:siRNA complexes based on the crystal structure of a short RNA fragment featuring a 3' two-residue overhang bound to the human Ago2 PAZ domain. This domain is most likely the only region of Ago2 affected by MePS2 modification near the siRNA 3'-end. Comparison of the complexes with siRNA and MePS2-siRNA reveals formation of a hydrophobic patch in the latter, that involves both the 2'-O-methyl and PS2 moieties as well as methionine and cysteine side chains from the PAZ domain (FIGS. 9A and B). FIGS. 9A and B depict models of the interactions between the human Ago2 PAZ domain and the (A) MePS2-modified and (B) native siRNA sense strands. Only the 3'-terminal five residues of the RNA are shown (n−5 to n) and the TT-overhang is visible on the upper right in both panels. The formation of a hydrophobic patch between the Met-273 and Cys-270 side chains, methoxy moiety of Gn-2 and PS2 of $T_{n-1}$ is highlighted with a dashed circle in FIG. 9A. PS2 groups, sulfur atoms (large pale balls) and 2'-O-methyl carbons are depicted in ball-and-stick mode and hydrogen atoms are white spheres of smaller radius. Note the significantly more polar environment of the phosphate (His, Tyr 2×, Lys) between overhanging dTs, visible on the right-hand side of the two panels.

The hypothesis that increased hydrophobicity conferred by the MePS2 modification plays a key role in the stronger binding to Ago2 and its enhanced efficacy is supported by the relative Ago2 affinities of siRNAs containing no modification, PS, MePS, PS2 or MePS2.

The MePS2 modification in the backbone region adjacent to the 3'-dTdT overhang of the siRNA sense strand triggers a strongly enhanced affinity to the RISC Ago2 slicer and silencing of proteins that confer chemoresistance in ovarian cancer cell lines and tumors. This finding is surprising given the fact that the antisense siRNA strand mediates cleavage of the target RNA at the Ago2 active site and indicates that chemical modification of the sense strand can play a key role in siRNA loading and efficacy. The PS2 moiety disrupts H-bonding interactions in the water chain bridging adjacent O2P atoms in the major groove.

We demonstrate here that MePS2 modification does not affect RNA conformation and stability. Instead the increased Ago2 affinity is likely the result of favorable hydrophobic interactions with the PAZ domain mediated by both the 2'-O-methyl and PS2 moieties. This conclusion is consistent with the inability of PS2 sulfur atoms to form H-bonds with water molecules lining the RNA backbone in the crystal structure.

Both steric and electronic factors can contribute to the increased nuclease resistance afforded by a modification. The bulkier sulfur atoms in the PS2 moiety along with the increased hydrophobicity relative to PO2 might exclude nonthiophilic metal ions (e.g. $Mg^{2+}$) from an exonuclease active site or result in suboptimal positioning of the water nucleophile for attack at the phosphate group.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A chemically modified siRNA directed to interference with a RISC Ago2 slicer associated with chemoresistance in ovarian cancer cell lines and tumors, wherein the chemical modifications to the siRNA comprise a combination of 2'-OMe and PS2 modifications on either or both sense and antisense strands of the siRNA that improve serum stability and gene silencing efficacy.

2. A chemically modified siRNA directed to interference with a GRAM Domain Containing 1B (GRAMD1B) associated with chemoresistance, wherein the chemical modifications to the siRNA comprise a combination of 2'-OMe and PS2 modifications on either or both sense and antisense strands of the siRNA that improve serum stability and gene silencing efficacy.

3. A combination therapy for cancer chemotherapy comprising a chemotherapeutic agent and a chemically modified siRNA that interferes with expression of a protein conferring resistance to the chemotherapeutic agent, wherein the chemical modifications to the siRNA comprise a combination of 2'-OMe and PS2 modifications on either or both sense and antisense strands of the siRNA that improve serum stability and gene silencing efficacy of the siRNA.

4. A method of improving serum stability and gene silencing efficacy of the siRNA directed to interference with a RISC Ago2 slicer associated with chemoresistance in ovarian cancer cell lines and tumors comprising introducing a combination of 2'-OMe and PS2 modifications on either or both sense and antisense strands of the siRNA and testing for improved serum stability and gene silencing efficacy of the siRNA.

5. A method of improving serum stability and gene silencing efficacy of the siRNA directed to interference with a GRAM Domain Containing 1B (GRAMD1B) associated with chemoresistance comprising introducing a combination of 2'-OMe and PS2 modifications on either or both sense and antisense strands of the siRNA and testing for improved serum stability and gene silencing efficacy of the siRNA.

6. The chemically modified siRNA of claim 1, wherein both sense and antisense-strands of the siRNA contain dTdT on their 3' terminus.

7. The chemically modified siRNA of claim 2, wherein both sense and antisense-strands of the siRNA contain dTdT on their 3' terminus.

8. The chemically modified siRNA of claim 3, wherein both sense and antisense-strands of the siRNA contain dTdT on their 3' terminus.

9. The chemically modified siRNA of claim 1 wherein a 3' end of the sense strand terminates in a sequence UGdTdT-3'.

10. The chemically modified siRNA of claim 2 wherein a 3' end of the sense strand terminates in a sequence UGdTdT-3'.

11. The chemically modified siRNA of claim 3 wherein a 3' end of the sense strand terminates in a sequence UGdTdT-3'.

12. The chemically modified siRNA of claim 1, wherein a length of either the sense or antisense strand is 21 nucleotides including the 3' dTdT.

13. The chemically modified siRNA of claim 2, wherein a length of either the sense or antisense strand is 21 nucleotides including the 3' dTdT.

14. The chemically modified siRNA of claim 3, wherein a length of either the sense or antisense strand is 21 nucleotides including the 3' dTdT.

15. The chemically modified siRNA of claim 1, wherein a total number of G+C of the sense strand are 9 nucleotides.

16. The chemically modified siRNA of claim 2, wherein a total number of G+C of the sense strand are 9 nucleotides.

17. The chemically modified siRNA of claim 3, wherein a total number of G+C of the sense strand are 9 nucleotides.

18. The chemically modified siRNA of claim 1, wherein the 2'-OMe and PS2 modifications are in a backbone region adjacent to a 3'-dTdT overhang of the siRNA sense strand.

19. The chemically modified siRNA of claim 2, wherein the 2'-OMe and PS2 modifications are in a backbone region adjacent to a 3'-dTdT overhang of the siRNA sense strand.

20. The chemically modified siRNA of claim 3, wherein the 2'-OMe and PS2 modifications are in a backbone region adjacent to a 3'-dTdT overhang of the siRNA sense strand.

* * * * *